United States Patent [19]
Miller

[11] Patent Number: 4,916,630
[45] Date of Patent: Apr. 10, 1990

[54] BED TESTER FOR MOLECULAR SIEVE OXYGEN CONCENTRATOR

[75] Inventor: George W. Miller, San Antonio, Tex.

[73] Assignee: The United States of America as represented by the Secretary of the Air Force, Washington, D.C.

[21] Appl. No.: 251,268

[22] Filed: Sep. 30, 1988

[51] Int. Cl.$^4$ .................. B01D 53/22; B01D 53/04
[52] U.S. Cl. ................... 364/496; 364/556; 55/75; 55/179; 55/21
[58] Field of Search ........... 364/496, 497, 498, 556; 73/23; 55/21, 25, 68, 75, 162, 163, 179, 389

[56] References Cited

U.S. PATENT DOCUMENTS

| | | | |
|---|---|---|---|
| 4,272,265 | 6/1981 | Snyder | 55/163 |
| 4,404,005 | 9/1983 | Hamlin et al. | 55/163 |
| 4,455,861 | 6/1984 | Alftine | 55/21 |
| 4,516,424 | 5/1985 | Rowland | 73/23 |
| 4,519,813 | 5/1985 | Hagiwara et al. | 55/75 |
| 4,561,287 | 12/1985 | Rowland | 73/23 |
| 4,576,616 | 3/1986 | Mottram et al. | 55/75 |
| 4,627,860 | 12/1986 | Rowland | 55/162 |
| 4,636,226 | 1/1987 | Canfora | 55/75 |
| 4,648,888 | 3/1987 | Rowland | 55/21 |
| 4,661,124 | 4/1987 | Hamlin et al. | 55/75 |
| 4,673,415 | 6/1987 | Stanford | 55/21 |
| 4,684,377 | 8/1987 | Haruna et al. | 55/75 |
| 4,685,939 | 8/1987 | Kratz et al. | 55/75 |
| 4,725,293 | 2/1988 | Gunderson | 55/162 |
| 4,756,723 | 7/1988 | Sircar | 55/75 |
| 4,822,384 | 4/1989 | Kato et al. | 55/179 |

Primary Examiner—P. S. Lall
Assistant Examiner—Christopher L. Makay
Attorney, Agent, or Firm—Bernard E. Franz; Donald J. Singer

[57] ABSTRACT

The bed tester includes nitrogen and helium sources, a scale, temperature and pressure readouts, and a computer program for determining the available adsorption capacity or activity of molecular sieve beds. Activity is a measure of the condition of the molecular sieve and is defined as the ratio of the weight of nitrogen adsorbed in the bed under test to the weight of nitrogen adsorbed by an equivalent weight of activated molecular seive. To determine the weight of nitrogen adsorbed for the bed under test, a chamber or plenum of known volume is filled with helium, and expanded into the bed. Then the helium is evacuated, and the bed is pressurized with nitrogen. Measured values of pressure, temperature and weight, and known values of volume and density, are used with the ideal gas law (PV=MRT) and other equations in calculations to arrive at the true weight gain due to nitrogen adsorption. Determining the weight of nitrogen adsorbed by an equivalent weight of activated molecular sieve is accomplished by using a set of pure crystal isotherm parameters for 5A and 13X zeolites, which are stored in a table. These parameters were determined by collecting pure crystal-N2 isotherm data for the zeolite crystals over the temperature range of 14–44 C. The data were then fit to a Sips equation by a least squres technique. The weight percent of water of the molecular sieve is calculated based on correlations with activity determined by a least square technique.

12 Claims, 3 Drawing Sheets

PRIOR ART

4,916,630

BED TESTER FOR MOLECULAR SIEVE OXYGEN CONCENTRATOR

RIGHTS OF THE GOVERNMENT

The invention described herein may be manufactured and used by or for the Government of the United States for all governmental purposes without the payment of any royalty.

BACKGROUND OF THE INVENTION

The present invention relates generally to a bed tester for molecular sieve oxygen concentrators.

Molecular sieve oxygen concentrators have become increasingly popular for the production of high purity oxygen (up to 95%) because of their simplicity, reduced energy consumption, and low operating costs. Portable units are now widely used to produce medical oxygen for patients requiring oxygen therapy. Molecular sieve oxygen concentrators are also in use aboard military aircraft for the production of an oxygen enriched breathing gas to prevent hypoxia. In addition, future military aircraft will have oxygen breathing systems employing molecular sieve oxygen concentrators. Oxygen concentrators may have from two to six beds filled with molecular sieve. For further background relating to molecular sieve oxygen concentrators and zeolites, see a copending patent application Ser. No. 07/151,383 filed Feb. 2, 1988, now Pat. No. 4,813,979 issued Mar. 21, 1989 to G. W. Miller and C. F. Theis, "Secondary Oxygen Purifier for Molecular Sieve Oxygen Concentrator", and the following papers: D. M. Ruthven, Sec. 1.4 on "Zeolites" in *Principles of Adsorption and Adsorption Process*, pages 9–16, John Wiley and Sons, New York, N.Y. (1984); G. W. Miller, Dr. K. G. Ikels, and P. A. Lozano, "Chemical Contamination Studies on a Molecular Sieve Oxygen Concentrator (MSOC): Comparison of MG3 and 5AMG Molecular Sieves", *Safe Journal*, Vol. 16 No. 4 (1986); D. E. W. Vaughan, "The Synthesis and Manufacture of Zeolites", Chemical Engineering Progress, February 1988, pages 25–31; D. M. Ruthven, "Zeolites as Selective Adsorbents, Chemical Engineering Progress, February 1988, pages 42–50; G. W. Miller, K. S. Knaebel, and K. G. Ikels, "Equilibria of Nitrogen, Oxygen, Argon, and Air in Molecular Sieve 5A", AIChE Journal, February 1987, Vol. 33, No. 2, pages 194–201; G. W. Miller, "Adsorption of Nitrogen, Oxygen, Argon, and Ternary Mixtures of These Gases in 13X Molecular Sieve", *American Institute of Chemical Engineers Symposium Series*, Vol. 83, No. 259, (1987) pages 28–39.

At present, most molecular sieve oxygen concentrators use 16×40 mesh type 5AMG or MG3 molecular sieves, having zeolite 5A and 13X crystals, respectively. The crystal structure has voids in the form of $\alpha$ cages and $\beta$ cages, as described in the above papers. Both nitrogen and oxygen are adsorbed in the large $\alpha$ cages of these zeolites, however, these crystals have a greater affinity for nitrogen due to its slight molecular polarity. Nitrogen and oxygen do not enter the smaller $\beta$ cages. Due to its small molecular size and nonpolarity, helium adsorbs in negligible quantities, and hence, enters the entire void volume of the zeolite crystals ($\alpha$ and $\beta$ cages).

The concentrator's performance or oxygen enriching ability is directly related to the activity of the molecular sieve. Further, the activity of a molecular sieve bed can be degraded by exposure to certain chemical species (principally water) resulting in a reduction in system performance. There is a need for a means for testing the molecular sieve beds to ensure they meet accepted standards of activity.

In the prior art, there are two methods used to determine the activity of a molecular sieve bed. The first method involves reactivating several samples of molecular sieve which have been removed from the bed. The second method involves determining the bed washout pattern using nitrogen and oxygen. Both methods have limitations and disadvantages which are discussed below.

Using the activation method one must remove several samples (3-5) of molecular sieve from the bed. Each sample must be heated to 350 C. for a period of at least four hours at a pressure of approximately one Torr. Based on the weight change of the sample one can calculate the amount of water removed, and therefore, arrive at a value for the weight percent water contained by the sample. The bed weight percent water is determined by averaging the results for all samples. Because bed activity is generally a function of the weight percent water one can arrive at a value for the activity. The limitations and disadvantages of this method are listed below.

1. The activation method requires disassembly of the molecular sieve bed for the removal of several samples. Disassembly and reassembly can be time consuming and must be performed by a skilled technician to ensure the bed is properly reassembled.

2. This method is labor and time intensive. In general, an activity test using this method would require approximately 6-8 hours per bed.

3. If the samples are not taken randomly, this method can give inaccurate results. These inaccuracies may occur because generally only 1-2% of the molecular sieve in the bed undergoes the test.

A schematic diagram of the apparatus required for the washout pattern technique is shown at FIG. 1 (See K. G. Ikels and C. F. Theis, *Aviation, Space, and Environmental Medicine*, 56: 33–6, 1985.). Using this technique, the molecular sieve bed is first flushed with oxygen via valves V1a, V3a, and V4a. Confirmation of a thoroughly flushed bed would be a 100% oxygen signal at a mass spectrometer 1a. The gas flow is then switched from oxygen to nitrogen via a valve V3a, and the oxygen washout pattern is recorded on a strip chart recorder 2a. A waveform of the nitrogen front exiting the bed is recorded and used to determine the activity of the molecular sieve. The lower the activity of the molecular sieve in the bed the shorter the time required for the nitrogen front to appear. Because washout time is a function of bed activity one can arrive at a value for the bed activity, if one has defined this relationship for the particular bed under test. The limitations and disadvantages of this technique are presented below.

1. Ideally this technique requires a mass spectrometer to analyze the concentration of nitrogen and oxygen in the flow. The cost of this unit is approximately $45,000–60,000. Hence, the cost of an apparatus for testing bed activity based on the washout pattern technique would be expensive.

2. The possibility of obtaining inaccurate values for the bed activity is likely due to the dynamic nature of the washout pattern technique. The results are highly dependent on:

a. The pressure upstream of valve V4a.

b. The steady-state flow setting.
c. The geometry of the particular bed under test.
d. The atmospheric pressure.
e. The diameter of the piping.
f. The response time of the mass spectrometer (if a unit other than a Perkin-Elmer MGA-1100 is employed).

Hence, reproducibility of the data between two apparatuses could be a problem.

3. Use of this technique would require the user to establish a relationship between the washout pattern and activity for each type of molecular sieve bed tested. This relationship would have to be accomplished by a skilled technician.

4. The washout pattern technique also requires a skilled technician to interpret the washout patterns.

United States patents of interest include No. 4,725,293 to Gunderson, which relates to automatic control for a pressure swing adsorption system which fractionalizes air to recover a high purity component. This patent discloses a preferred embodiment in which comparator-controllers are implemented by a microprocessor based programmable controller using software provided therewith which includes Proportional-Integral and Derivative (P-I-D) control algorithms. See, for example, col. 8, line 44 et seq., col. 12, line 4 et seq. and appendix A.

Pat. No. 4,648,888 to Rowland relates to an oxygen concentrator and discloses a controller having a microprocessor which may be programmed to change the sieve bed and/or surge tank charge times to maintain desirable oxygen conentrations in the product gas. Similarly see Pat. No. 4,561,287 to Rowland.

Pat. No. 4,627,860 to Rowland relates to an oxygen concentrator and test apparatus having means for selecting any of the functions monitored by the microprocessor. The test apparatus is connected to the concentrator and displays the selected monitored functions for diagnosing performance levels and component problems or failures. Pat. No. 4,404,005 to Hamlin et al relates to a breathable gas supply for aircrew in a pressurized cabin, comprising a control system based upon a microprocessor which can incorporate a self-test facility. Pat. No. 4,272,265 to Snyder describes apparatus for generating oxygen by the pressure swing method. The apparatus is comprised of a plurality of vessels each having a molecular sieve bed.

SUMMARY OF THE INVENTION

An object of the invention is to provide a quick, accurate, and cost-effective means for determining the available adsorption capacity or activity of molecular sieve oxygen concentrator beds, for ensuring that the molecular sieve beds meet accepted standards of activity.

Activity is a measure of the condition of the molecular sieve and is defined herein as, $$\text{Activity} = \frac{\text{Wt. of Nitrogen Adsorbed in the Bed Under Test}}{\text{Wt. of Nitrogen Adsorbed by an Equivalent Wt. of Activated Molecular Sieve}} (100)$$

The invention provides an apparatus and method for determining the activity, using a bed tester unit (which includes nitrogen and helium sources, a helium chamber of plenum, a scale and temperature and pressure readouts) and a computer program.

Determining the weight of nitrogen adsorbed for the bed under test includes pressurizing the bed from a pure nitrogen source, and weighing the bed before and after to provide a measure of the weight gain. Nitrogen is adsorbed in the large alpha cages of the zeolite crystals. In addition nitrogen fills the void volume of the molecular sieve pellets. Hence, the weight of the gas in the void volume must be subtracted to find the true weight gain due to adsorption. The ideal gas law ($PV = MRT$) is used a number of times in the calculations to find the weight of the nitrogen gas in the void volume. First, a chamber or plenum of known volume is filled with helium, and expanded into the bed. Then the helium is evacuated, and the bed is pressurized with nitrogen. Measured values of pressure, temperature and weight, and known values of volume and density, are used with the gas law and other equations in calculations to arrive at the true weight gain due to nitrogen adsorption.

Determining the weight of nitrogen adsorbed by an equivalent weight of activated molecular sieve is accomplished by using a set of pure crystals isotherm parameters, which are stored in a table. These parameters were determined by the applicant by collecting pure crystal-N2 isotherm data for the zeolite crystals over the temperature range of 14–44 C. The data were then fit to a Sips equation by a least squares technique.

The weight percent of water of the molecular sieve is calculated based on correlations with activity determined by a least squares technique. These correlations were determined by the applicant.

The bed tester and method according to the invention could be used in the following ways:

1. Molecular sieve beds could be tested as they leave the manufacturer's production line. This would ensure molecular sieve beds meet an acceptable activity specification before installations on newly manufactured concentrators.

2. Molecular sieve beds already in service could be tested periodically (possibly during aircraft phase inspections) to ensure they meet minimum specifications. This testing would also provide a convenient means for tracking the activity of the bed during the molecular sieve's life.

3. Molecular sieve replacement beds taken from storage could be tested before installation to ensure that the activity of the molecular sieve had not degraded in storage.

ADVANTAGES AND FEATURES

Advantages and features of the invention include the following:

1. The activity and equivalent weight percent water of a molecular sieve bed is determined based on the bed weight change during nitrogen adsorption.

2. The apparatus can be constructed for less than $4,000.

3. The bed activity can be determined in 6–15 minutes.

4. The activity of any type of concentrator bed can be determined. The only information required for each type of bed is the volume occupied by the molecular sieve pellets.

5. Correlations technique developed by the applicant (G. W. Miller) are used to determine the equivalent weight percent water.

6. The apparatus and computer program for practicing the invention can be operated by individuals with litte or no training.

7. The activity test is conducted on the entire contents of the molecular sieve bed.

8. The adsorption capacity of pure molecular sieve crystals is the standard used for determination of activity.

DETAILED DESCRIPTION

In general, the activity of a molecular sieve bed degrades upon exposure to certain chemical species (especially water). In most cases this degradation in activity occurs at a slow rate, however, if the molecular sieve were exposed to liquid phase water, due to condensation or feed air water separator failure, the degradation could be significant. A degradation in molecular sieve activity results in a reduction in concentrator performance and contaminant removal ability. The use of the method and apparatus according to the invention provides reproducible information on the exact condition of the molecular sieve material. With this information one can set minimum acceptable specifications for bed activity, and hence, use this specification as a guideline for bed replacements, thereby, ensuring consistent performance of oxygen concentrators.

Figure 1:
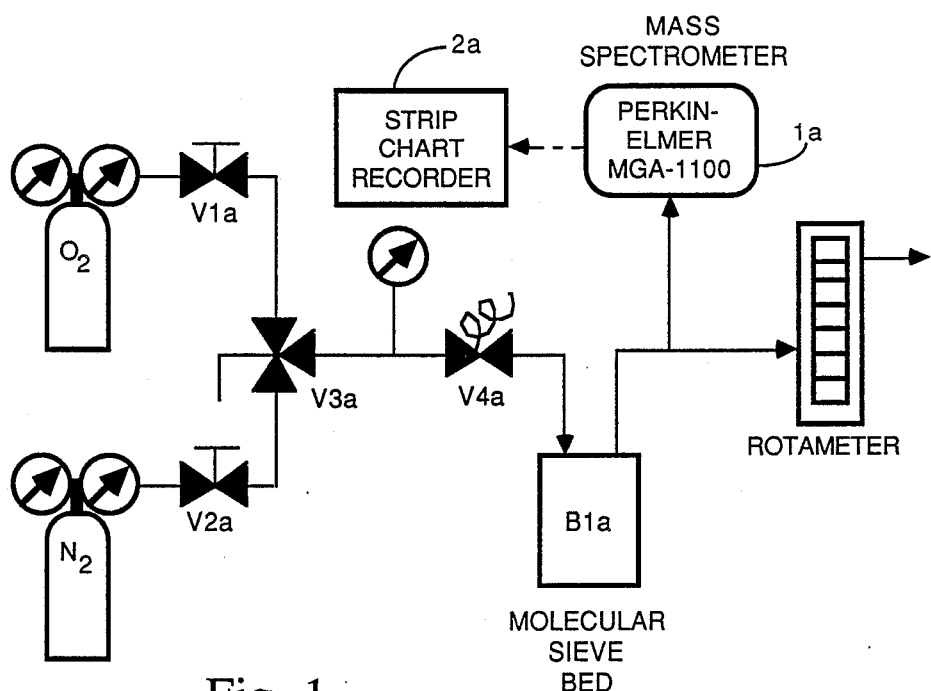
FIG. 1 is a block and schematic diagram showing apparatus required for a prior art technique to determine a washout pattern.
Figure 2:
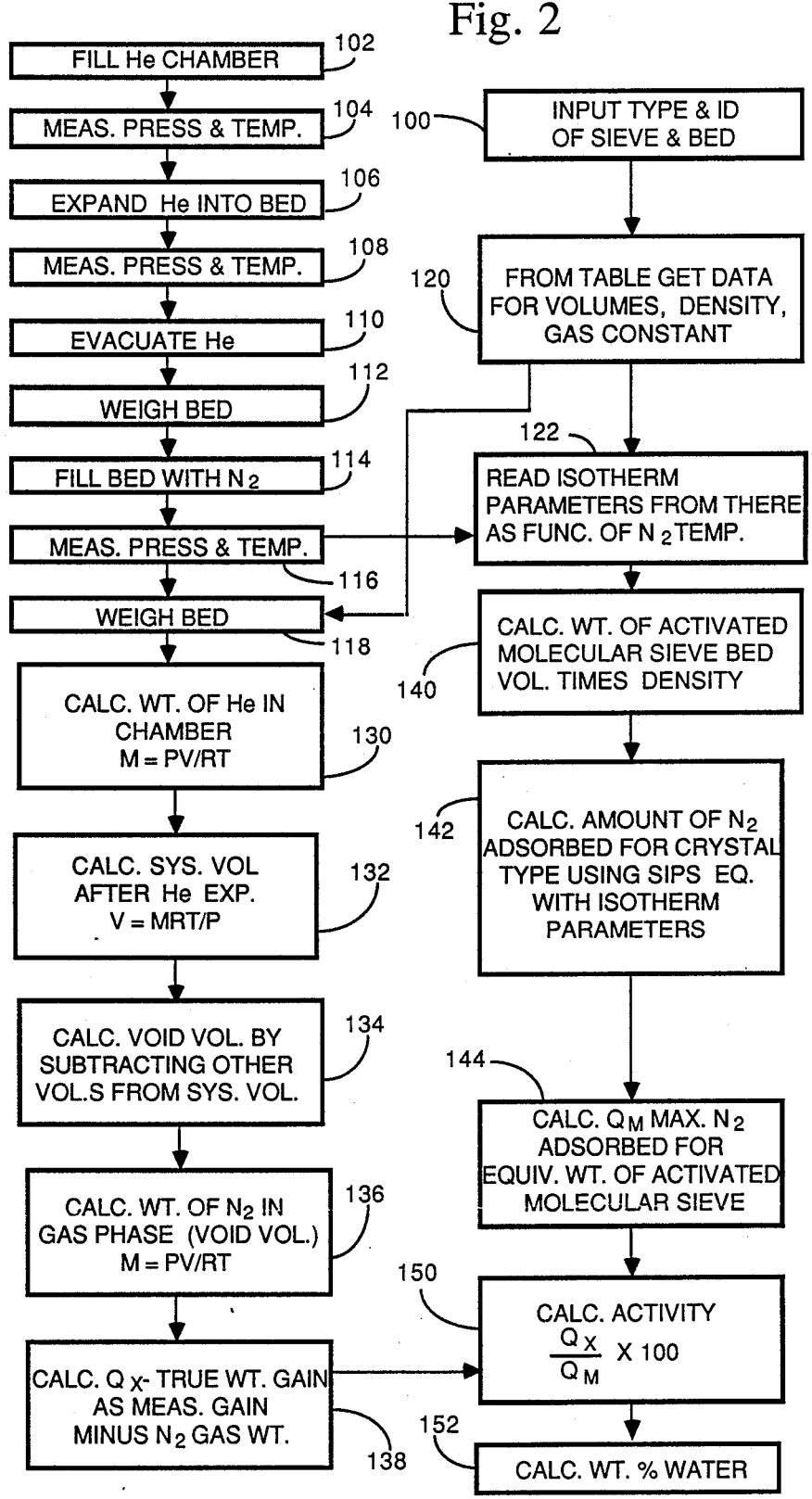
FIG. 2 is a flow chart.

The basic steps and elements relating to the invention are illustrated by a flow chart of FIG. 2. Bed tester apparatus (which includes nitrogen and helium sources, a scale and temperature and pressure readouts) is used in steps shown by blocks 102-118. A computer program is preferably used to perform calculations shown in blocks 130-152. Predetermined values for data and constants are shown in the chart as tables in blocks 120 and 122, which are preferably included in the computer program. Broadly speaking, the tables and formulas for the calculations could be simply provided on paper.

As stated above, the basic principle of the invention is to determine the activity of molecular sieve beds by finding the ratio of the weight of nitrogen adsorbed for a bed under test, shown in block 138 as $Q_X$, to the weight of nitrogen adsorbed for an equivalent weight of activated molecular sieve, shown in block 144 as $Q_M$. The ratio $Q_X/Q_M$ is shown as being formed in block 150.

Determining the weight of nitrogen adsorbed for the bed under test includes pressurizing the bed from a pure nitrogen source, and weighing the bed before and after to provide a measure of the weight gain. Nitrogen is adsorbed in the large alpha cages of the crystals and gas phase nitrogen fills the void volume of the molecular sieve pellets. The weight of this gas in the void volume needs to be subtracted to find the true weight gain. The ideal gas law (PV=MRT) is used a number of times in the calculations to find the weight of the nitrogen gas in the void volume. First, referring to blocks 102-110, a chamber or plenum is filled with helium, the initial pressure and temperature are measured, the helium is expanded into the bed, the final helium pressure and temperature are measured, and the helium is evacuated.

As shown at blocks 110-118, the bed is now weighed for a tare value, it is pressurized with nitrogen, the pressure and temperature are measured, and the bed is weighed again to determine the weight gain.

The ideal gas law is used first at block 130 to calculate the mass of the helium (M=PV/RT) using the initial values of pressure and temperature measured at step 104, with the chamber volume and the gas constant from the table 120. This value of mass is used at block 132 to calculate the total system volume (V=MRT/P) using the final helium pressure and temperature measured at step 108. At block 134 the void volume is determined by subtracting values from table 120 for volumes of the chamber, some connecting tubing, and the beta cages from the system volume. This void volume is used at block 136 along with the nitrogen pressure and temperature measured at step 116 to calculate the weight (M=PV/RT) of nitrogen in the gas phase. At block 138 this weight is deducted from that measured at step 118 to obtain the true weight gain due to nitrogen adsorption.

Determining the weight of nitrogen adsorbed by an equivalent weight of activated molecular sieve is accomplished by using a set of pure crystal isotherm parameters, which are stored in a table read at block 122. These parameters were determined by applicant (G. W. Miller) by collecting pure crystal-N2 isotherm data for 5A and 13X zeolite crystals over the temperature range of 14–44 C. The data were then fit to a Sips equation (shown below) (see Sips, R. J., J. Chem. Phys., 16, 490 (1948)) by a least squares technique.

$$q = \frac{ap^c}{1 + bp^c}$$

where,
q=amount adsorbed
p=pressure
a, b, and c=parameters to be determined by least squares analysis To read the isotherm parameters at step 122, the value of nitrogen temperature measured at step 116 is used.

The weight of activated molecular sieve is calculated at block 140 using values of bed volume and density from the table at block 120, and using the product of these values. At block 142 the Sips equation is used with the isotherm parameters a, b and c read from the table at step 122 to calculate the amount of nitrogen adsorbed. At block 144 the maximum amount of nitrogen adsorbed for the equivalent weight of activated molecular sieve is calculated using the results from steps 140 and 142. The activity and weight percent of water are now calculated at steps 150 and 152.

The weight percent of water of the molecular sieve is determined based on correlations with activity which were developed by applicant. The correlations for 5AMG and MG3 were determined by a least squares technique and are presented below.

5AMG: Y = −1.9621500 + 23.338246889 * EXP (−0.024760528*X)

MG3: Y = −0.7140699 + 29.679412844 * EXP (−0.037272280*X)

where,
Y=weight percent water
X=activity

Calculations

The calculations of blocks 130–152 are given below as a set of equations. The nomenclature or definition of terms used in the equations is listed first with the symbol used in the equations in the first column, a FORTRAN name in the second column, the definition in the third column, and the units in the fourth column. The units of pressure are pounds per square inch (psia), atmospheres (atm), and torrs (mm of Hg). The units of temperature are degrees centigrade (C.) and degrees Kelvin (K.). The units of volume are millimeters (ml) and liters. The units of weight and mass are grams (gm) and gram moles (moles). The units for some amounts are millimeters per gram at standard temperature (zero degrees C.) and pressure (one atmosphere) (ml STP/gm). The FORTRAN names for pellets and crystal are given in the second column only for type 5AMG pellets and 5A crystal.

Pressure

| | | | |
|---|---|---|---|
| $P_{hia}$ | PINIHE | Initial helium chamber press. | psia |
| $P_{hi}$ | XPINIHEX | " | atm |
| $P_{hfa}$ | PFINHE | Final helium press. for sys. | psia |
| $P_{hf}$ | XPFINHEX | " | atm |
| $P_{na}$ | PFINN2 | Final bed press. with N2. | psia |
| $P_{nb}$ | XPFINN2X | " | atm |
| $P_n$ | TPFINN2T | " | torr |

Temperature

| | | | |
|---|---|---|---|
| $T_{hia}$ | ITINIHE | Initial helium chamber temp. | C |
| $T_{hi}$ | TINIHE | " | K |
| $T_{hfa}$ | ITFINHE | Final helium temp. for sys. | C |
| $T_{hf}$ | TFINHE | " | K |
| T | ITFINN2 | Final bed temp. with N2. | C |
| $T_n$ | TFINN2 | " | K |

Volume

| | | | |
|---|---|---|---|
| $V_b$ | BEDVOL | Molecular sieve bulk vol. | ml |
| $V_{hia}$ | VHECHAM | Helium chamber vol. | ml |
| $V_{hi}$ | " | " | liter |
| $V_{ca}$ | VCONN | Bed tubing vol. | ml |
| $V_c$ | " | " | liter |
| $V_{vh}$ | VVOIDHE | Void vol. of bede including β-cages. | liter |
| $V_\beta$ | VBETA | Vol. of β-cages. | liter |
| $V_v$ | VVOID | Void vol. of sys excluding β-cages. | liter |
| $V_x$ | VB5AC | Void vol. of β-cages for 5A crystal. | ml/gm |
| $V_t$ | VTOTAL | Total void volume of system. | liter |

Mass (Weight)

| | | | |
|---|---|---|---|
| $W_x$ | WT5AMG | Weight of activated molecular sieve | gm |
| $W_n$ | WTN2GAS | Weight of N2 in gas phase. | gm |
| $M_n$ | XNN2GAS | Moles of N2 in gas phase. | moles |
| $\Delta W_a$ | DELWT | Weight gain after N2 adsorption. | gm |
| $\Delta W_b$ | " | True weight gain due to N2 adsorption. | gm |
| $\Delta W$ | XNN2ADS | True weight gain due to N2 adsorption. | moles |
| $M_h$ | XNHE | Moles of He. | moles |

Amounts

| | | | |
|---|---|---|---|
| $Q_n$ | Q5AC | Amount of N2 adsorbed in crystal. | ml STP/gm |
| $Q_X$ | Q5AMG | Amount of N2 adsorbed in bed. | ml STP |
| $Q_M$ | QMAX | Amount of N2 adsorbed by an equivalent wt. of activated molecular sieve. | ml STP |

Other

| | | | |
|---|---|---|---|
| a | P15Ac(T) | Parameter from Sips equation. | |
| b | P25AC(T) | " | |
| c | P35AC(T) | " | |
| ρ | RHO5AMG | Bulk density of pellets | gm/ml |
| R | R | Gas constant (0.0821) | atm. liter mole °K |
| X | ACT | Activity | percent |
| Y | WATER | Weight percent water | percent |

Equations $$W_x = V_b \cdot \rho \quad (1)$$
$$P_{hi} = P_{hia}/14.7 \quad (2)$$
$$P_{hf} = P_{hfa}/14.7 \quad (3)$$
$$T_{hi} = T_{hia} + 273.15 \quad (4)$$
$$T_{hf} = T_{hfa} + 273.15 \quad (5)$$
$$V_{hi} = V_{hia}/1000 \quad (6)$$
$$V_c = V_{ca}/1000 \quad (7)$$
$$M_h = (P_{hia} \cdot V_{hi})/(r \cdot T_{hi}) \quad (8)$$
$$V_t = (M_h \cdot R \cdot T_{hf})/P_{hf} \quad (9)$$
$$V_{vh} = V_t - V_{hi} - V_c \quad (10)$$
$$V_\beta = (W_x \cdot 0.8 \cdot V_x/1000) \quad (11)$$
$$V_v = V_{vh} - V_\beta \quad (12)$$
$$Q_n = (a \cdot P_n^c)/(1 + b \cdot P_n^c) \quad (13)$$
$$P_n = (P_{na}/14.7) \cdot 760 \quad (14)$$
$$T_n = T + 273.15 \quad (15)$$
$$M_n = (P_{nb} \cdot V_v)/(R \cdot T_n) \quad (16)$$
$$W_n = M_n \cdot 28.0134 \quad (17)$$
$$\Delta W_b = \Delta W_a - W_n \quad (18)$$
$$\Delta W = \Delta W_b / 28.0134 \quad (19)$$
$$Q_X = (\Delta W \cdot R \cdot 273.15) \cdot 1000 \quad (20)$$
$$Q_M = Q_n \cdot W_x \cdot 0.8 \quad (21)$$
$$X = (Q_X / Q_M) \cdot 100 \quad (22)$$
$$Y = -1.96215 + 23.338246889 \cdot e(-0.024760528 \cdot X) \quad (23)$$

Description of the Preferred Embodiment

At present an embodiment of the invention has the following specifications:

1. The types of molecular sieves which can be tested are shown below. It should be noted that with minor additions to the FORTRAN program any molecular sieve could be tested using this apparatus.
   a. Union Carbide MG3 (16×40) Mesh.
   b. Union Carbide 5AMG (16×40) Mesh.
2. The types of molecular sieve oxygen concentrator beds which can be tested are listed below. It should also be noted that with very minor addition to the FORTRAN program any type of bed could be tested using this apparatus.
   a. Normalair-Garrett 3-bed prototype.
   b. Clifton Precision 2-bed prototype.
   c. Normalair-Garrett 6-bed B1-B concentrator
3. Temperature range: 14–44 C.
4. Weight range of the bed under test: up to 12 Kg.

The bed weight range could be increased by utilizing a different scale. However, it is recommended that the scale have a 0.1 g accuracy.

Maximum pressure applied during the activity test: 60 psia.

Figure 3:
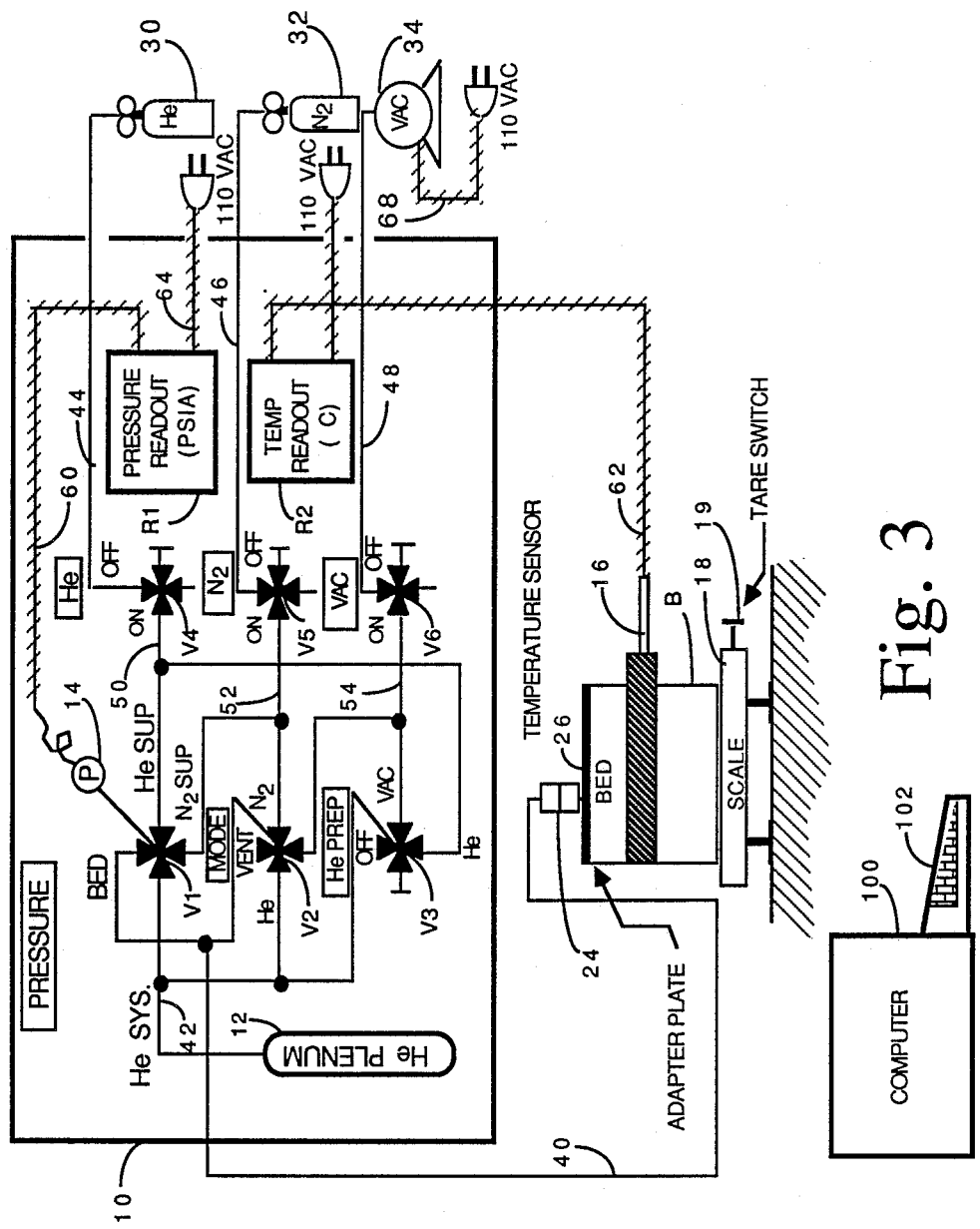
FIG. 3 is a block and schematic diagram showing bed tester apparatus according to the invention.

FIG. 3 is a block and schematic diagram showing bed tester apparatus, and a FORTRAN program listing is provided in Appendix I. The FORTRAN program provides instructions to the user for accomplishing the bed testing procedure and quickly calculates the bed activity and the bed weight percent water. The inputted parameters and final results are displayed on a screen and stored in a data file. The activity calculation is based on seven parameters inputted by the user: initial helium pressure, initial helium temperature, final helium pressure, final helium temperature, final bed pressure, final bed temperature, and the bed weight gain. The program is run on a computer shown in FIG. 3 as block 100 having a keyboard 102, which at present may be a Zenith personal computer (Z-100 or Z-248) or a Digital Equipment Corporation VAX computer (such as the VAX 11/780). The names of the three functionally identical programs are shown below.

TEST100.EXE: Runs on the Zenith Z-100 personal computer.

TEST248.EXE: Runs on the Zenith Z-248 personal computer.

TESTVAX.EXE: Runs on the DEC VAX computers.

The program will perform a bed activity test on the following molecular sieves and oxygen concentrator beds over the temperature range of 14-44 C.

Molecular sieves:
Union Carbide (16×40) Mesh 5AMG.
Union Carbide (16×40) Mesh MG3.
Beds from the following concentrators may be tested:
3-Bed Normalair-Garrett Ltd. Prototype.
2-Bed Clifton Precision Prototype.
6-Bed Normalair-Garrett Ltd. B1-B Aircraft Unit Beds from other concentrators and beds containing other types of molecular sieves could be tested with only minor modifications to the program.

The apparatus used in conjunction with the FORTRAN program is shown in FIG. 3. The bed test is comprised of three 5-way valves V1, V2 and V3, three 4-way manual valves V4, V5 and V6, a helium storage chamber or plenum 12, a pressure transducer 14, a temperature sensor 16, a digital scale 18 which has a tare switch 19, a digital pressure readout unit R1, and a digital temperature readout unit R2. Valve V1 is a "PRESSURE" valve, valve V2 is a "MODE" valve and valve V3 is a "He PREP" valve. The valves V4–V6 are on-off valves for the helium, the nitrogen and the vacuum, respectively. The scale 18 has an accuracy of 0.1 gram. The bed tester apparatus is interfaced to the bed B under test by a quick disconnect connector 24 (SwageLock Fittings Model QF4-B-316 and QF4-S-316) and an adapter plate 26. The tester apparatus requires a source of high purity bottled helium shown as a tank 30, a source of high purity bottled nitrogen shown as a tank 32, and a vacuum source shown as a pump 34.

The apparatus includes tubing which inside the box 10 is ¼" O.D. stainless steel, and outside the box 10 in four places is ¼" flexible tubing. The bed B is coupled via the connector 24 and tubing 40 to the valves V1 and V2. The helium plenum 12 is coupled via tubing 42 to the valves V1, V2 and V3. The valves V4, V5 and V6 are connected via tubing 44, 46 and 48 respectively to the sources 30, 32 and 34. Valve V4 is coupled via tubing 50 to valves V1 and V3. Valve V5 is coupled via tubing 52 to valves V1 and V2. Valve V6 is coupled via tubing 54 to valves V2 and V3.

The valve V1 provides for connecting the pressure sensor selectively to the helium supply, the nitrogen supply, the helium system, or the bed. The valve V3 provides for connecting the bed B selectively to the nitrogen supply, the vacuum source, the helium system, or to a vent. The valve V3 provides for connecting the helium system selectively to the vacuum source, the helium supply, or an OFF position.

Electrical connections include line 60 from the pressure transducer 14 to the pressure readout unit R1, and line 62 from the temperature sensor 16 to the temperature readout unit R2. Lines 64, 66 and 68 are used to supply power at 110 volts AC to the pressure readout unit R1, the temperature readout unit R2 and the vacuum pump 34, respectively.

The parts in FIG. 3 may be models as follows:
1. Valves V1 and V3 are Whitey 5-way valves (SS-43ZF2).
2. Valve V2 is Whitey 5-way valve (B-43ZF2-00125).
3. Valves V4–V6 are Whitey 4-way valves (SS-43YF2).
4. Temperature sensor 16 is Omega type K surface thermocouple.
5. The pressure readout unit R1 was fabricated by USAFSAM.
6. The temperature readout unit R2 is Cole-Parmer Model 8534-1.
7. The scale 18 is Sartorius Model E12000S or equivalent.
8. The vacuum pump 34 is Duo-Seal Model 1376 or equivalent.
9. The pressure transducer 14 is Statham Pressure Sensor Model PA208TC-50-350, or equivalent.

Note that a dictionary definition of "plenum" is an enclosed volume of gas under greater pressure than that surrounding the container. After pressurization from the tank 30, the plenum of helium exists in a volume of space in the container 12 and the tubing 42.

The Operation

The following is a step-by explanation of how one uses the bed tester apparatus of FIG. 3 and the FORTRAN program of Appendix I to perform an activity test on a molecular sieve bed.

1. The source of 55–60 psia helium from tank 30 and nitrogen from tank 32 is applied to the upper port of valves V4 and V5, respectively. A vacuum source 34 is applied to the upper port of valve V6. The vacuum pump 34 used had a rated capacity of 10 CFM.

2. The appropriate program is loaded and run on the computer 100.

At the beginning of the program under the comment "DATA", some parameter values are given, which are part of the table shown in FIG. 2 at block 120. The universal gas constant R is given for pressure in atmospheres, volume in liters, mass in moles, and temperature in degrees Kelvin. The following parameters were determined by applicant (G. W. Miller). The volumes in the bed tubing and in the helium chamber are given. The bulk densities, for MG3 and 5AMG pellets are given. The values for the volume of the molecular sieve beta cages are given for 13X and 5A crystal.

3. The program (lines 10 and 17) requests the user to enter the date and time of day.

4. The program (line 50) requests the user to select a type of molecular sieve from the list shown below.
a. 5AMG (Union Carbide 16×40 Mesh)

b. MG3 (Union Carbide 16×40 Mesh)

5. The program (line 110) requests the user to enter the molecular sieve bed identification number.

6. The program (line 130) requests the user to choose the type of concentrator from the following list.
   a. NGL 3-Bed Prototype.
   b. Clifton 2-Bed Prototype.
   c. NGL B-1B unit.

(Steps 3-6 are represented in FIG. 2 as block 100.)

7. The program assigns a value to the parameter BEDVOL based on the type of concentrator chosen. BEDVOL is the volume occupied by the molecular sieve pellets within the bed. Values of BEDVOL are stored in the program for the three types of beds shown above.

8. The program (line 180) requests the user to initialize the bed tester 10 of FIG. 3:
   PRESSURE selector: "BED"
   MODE selector: "VENT"
   HE PREP selector: "OFF"
   HE selector: "OFF"
   N2 selector: "OFF"
   VAC selector: "OFF"

Place bed on bench and connect to the bed tester with the connector 24.

Do not install the temperature probe 16 on the bed.

The Pressure selector valve V1 is rotated to the "BED" position. The MODE selector valve V2 is rotated to the "VENT" position. The HE PREP selector valve V3 is rotated to the "OFF" position. The HE selector valve V4 is confirmed in the "OFF" position. The N2 selector valve V5 is confirmed in the "OFF" position. The VAC selector valve V6 is confirmed in the "OFF" position. The bed under test with the adapter plate 26 installed is placed on the bench. The user is requested not to install the temperature probe 16 at this time.

9. The user is requested:
   HE selector to "ON" (line 190)
   N2 selector to "ON"
   VAC selector to "ON"

The HE selector valve V4 is rotated to the "ON" position. The N2 selector valve V5 is rotated to the "ON" position. The VAC selector valve V6 is rotated to the "ON" position.

10. Rotate the Pressure selector valve V1 CLOCKWISE to "HE SUP" and ensure that the Pressure Readout on unit R1 indicates 55-60 psia (line 200). The pressure indicated is that of the helium supply source 30.

11. Rotate the Pressure selector valve V1 CLOCKWISE to "N2 SUP" and ensure that the Pressure Readout on unit R1 indicates 55-60 psia (line 210). The pressure indicated is that of the nitrogen supply source 32.

12. Rotate the Pressure selector valve V1 CLOCKWISE to the "HE SYS" position (line 220).

13. Rotate the HE PREP selector valve V3 CLOCKWISE to "VAC" and wait until the Pressure readout on unit R1 indicates 00.1 psia (line 230). In this step the gas in the helium plenum 12 is removed until a pressure of at most 0.1 psia is achieved.

14. Rotate the HE PREP selector valve V3 CLOCKWISE to the "HE" position (line 240). The helium plenum 12 is filled with helium to a pressure between 55-60 psia (block 102 of FIG. 2).

15. Rotate the HE PREP selector valve V3 CLOCKWISE to the "OFF" position (line 250).

16. The program (line 260) requests the user to enter the Pressure Readout value. This parameter, PINIHE, represents the initial helium pressure.

17. The program (line 270) requests the user to enter the Temperature Readout value from the temp. readout unit R2. This parameter, ITINIHE, represents the initial helium temperature. Note that the sensor 16 is not in the bed B at this time, so the ambient temperature is read, which should be the initial helium temperature.

(Steps 16 and 17 are shown in FIG. 2 as block 104).

18. Rotate the Pressure selector valve V1 CLOCKWISE to the "BED" position (line 280).

19. Rotate the MODE selector valve V2 CLOCKWISE to the "VAC" position and wait until the Pressure readout on unit R1 indicates 01.0 psia (line 290). In this step the gas in the molecular sieve bed under test is evacuated to a pressure of at most 1.0 psia.

20. the surface temperature probe 16 is then installed at approximately the bed midpoint (line 300).

21. Rotate the MODE selector valve CLOCKWISE to the "HE" position (line 310). The as in the helium plenum 12 will expand into the bed B1 under test (block 106 of FIG. 2).

22. The program (line 320) requests the user to enter the Pressure Readout value. This parameter, PFINHE, represents the final helium pressure in the bed B1 and the helium plenum 12.

23. The program (line 330) requests the user to enter the Temperature Readout value. This parameter, ITFINHE, represents the final helium temperature.

(Steps 22 and 23 are shown in FIG. 2 as block 108).

24. Rotate the MODE selector valve V2 COUNTERCLOCKWISE to the "VAC" position and wait until the Pressure readout on unit R1 indicates 01.0 psia (line 340). In this step the helium is removed from the bed (block 110 of FIG. 2).

25. Place the bed B1 on the scale 18 and wait 60 seconds for the scale stabilization (line 341) (block 112 of FIG. 2).

26. Press the scale TARE switch 19 (line 350).

This step resets the scale digital display to zero. Rotate the MODE selectove valve V2 COUNTERCLOCKWISE to the "N2" position and wait until the Pressure Readout stabilizes. In this step the evacuated bed is pressurized with nitrogen to 55-60 psia (block 114 of FIG. 2).

27. The program (line 360) requests the user to enter the Pressure Readout value. This parameter, PFINN2, is the final bed pressure.

28. The program (line 370) requests the user to enter the Temperature Readout value. This parameter, ITFINN2, represents the final bed temperature.

(Steps 27 and 28 are shown in FIG. 2 as block 116).

29. The program requests the user to enter the scale Weight Readout value. This parameter, DELWT, represents the weight gain of the bed after pressurization with nitrogen.

30. The program (line 390) then guides the user through the bed tester shutdown procedure.
   Rotate the MODE selector valve V2 COUNTERCLOCKWISE to "VENT".
   Rotate the HE selector valve V4 to "OFF".
   Rotate the N2 selector valve V5 to "OFF".
   Rotate the VAC selector valve V6 to "OFF".
   Remove the bed B1 from the scale 18.
   Remove and store the temperature sensor 16.
   Press the TARE switch 19 on the scale 18.

Rotating the MODE selector valve V2 to "VENT" will depressurize the bed B1. Rotating the HE, N2, and VAC selector valves V4, V5, and V6 to "OFF" will isolate the helium, nitrogen, and vacuum sources, and vent the lines downstream to atmospheric pressure.

31. The next section of the program is the table of the 13X and 5A pure crystal isotherm parameters (block 122 of FIG. 2), giving the values of the three parameters of the Sips equation for each crystal type, for even values of temperature in the range of 14–44 C.

Following the comment "CALCULATIONS", there is first a test to determine whether the nitrogen temperature is within range, and then there are two sections of code, one immediately following for type 5AMG molecular sieve, and one starting at line 1000 for type MG3 molecular sieve, which are the same except for parameters relating to the sieve type. In the following description it will be assumed that the bed under test has type 5AMG sieve. Equations numbers will be given from the equations previously listed.

32. The program calculates the weight of molecular sieve pellets within the bed, WT5AMG, based on the bulk densities for the molecular sieve (Equation 1).

33. the total void volume of the bed and helium plenum, VTOTAL, is calculated (equations 2-19, inclusive, and blocks 130, 132 and 134 in FIG. 2) based on the user inputted parameters. The ideal gas law is employed in this calculation. The void volume of the bed is determined by subtracting the helium plenum volume and tester connection hose volume from the total void volume (equation 10). The cumulative volume of the molecular sieve beta cages is calculated based on the parameter VB5AC. The corrected void volume for adsorption, VVOID, is calculated by subtracting the volume of the beta cages from the void volume of the bed (equations 11 and 12).

Before using the gas law, some unit conversions are required. The helium pressures are converted from pounds/inch$^2$ to atmospheres by dividing by 14.7. The helium temperatures are converted from centigrade to Kelvin by adding 273.15. The volumes of the helium chamber and connections are converted from milliliters to liters by dividing by 1000. The gas law is used first in the form ($M = PV/RT$) using the initial helium pressure and temperature (before expansion into the bed) and the chamber volume to obtain a value for the mass of the helium in moles, and then in the form ($V = MRT/P$) using the final helium pressure and temperature (after expansion into the bed) to obtain the total void (system) volume.

34. The amount of nitrogen adsorbed per gram of pure crystal 5A molecular sieve type Q5AC is calculated based on the Sips equation (equations 13-15 and block 142 in FIG. 2) for the final bed temperature, ITFINN2. (This involves DO loops ending at lines 410 and 412, and calculations starting at lines 413 and 411. The program provides for interpolation between values given in the isotherm table.)

35. The weight of nitrogen gas filling the bed void volume, WTN2GAS, after pressurization is calculated (equations 16 and 17, line 420 et seq., and block 136 of FIG. 2).

36. The true weight gain of the bed due to nitrogen adsorption during pressurization is calculated by subtracting the parameter, WTN2GAS, from DELWT (eq. 18, and block 138 of FIG. 2).

37. The total amount of nitrogen adsorbed by the bed, Q5AMG, and the total amount of nitrogen adsorbed for an identical weight of activated molecular sieve, QMAX, is calculated (equations 19-21). The parameter QMAX is corrected to account for the twenty weight percent binder content of the molecular sieve pellets. (Blocks 138 and 144 of FIG. 2).

38. The activity of the molecular sieve in the bed under test is calculated by dividing QMAX into QMG3 or Q5AMG and multiplying by 100 (eq. 22, and block 150 of FIG. 2).

39. The program calculates the weight percent water of the molecular sieve, WATER, based on the activity parameter, ACT (eq. 23, and block 152 of FIG. 2).

40. The user inputted parameters and calculated results are displayed to the user and written to a data file, TESTER.DAT (lines 2000 et seq.). An example of the generated results is found in Appendix II. The information displayed to the screen and written to the data file is listed below:
  a. Date
  b. Time
  c. Bed identification number
  d. Type of concentrator
  e. Type of molecular sieve
  f. Initial helium pressure
  g. Initial helium temperature
  h. Final helium pressure
  i. Final helium temperature
  j. Final bed pressure
  k. Final bed temperature
  l. Weight gain
  m. Bed activity (accuracy: ±1%)
  n. Equivalent weight percent water
  o. A message indicating whether the bed passed or failed the activity test In item (n) above, the weight percent water of the bed is presented as the equivalent weight percent water. In nearly all cases these parameters are the same. However, one should be aware species other that water can degrade the performance of molecular sieve.

41. A message at the end of the generated results indicates whether the bed passed or failed the activity test. The messages which will appear are presented below:
  a. MOLECULAR SIEVE ACTIVITY IS ACCEPTABLE
     EQUIVALENT WEIGHT PERCENT WATER LESS THAN OR EQUAL TO 2.5%
     ///// BED PASSED TEST /////
  b. MOLECULAR SIEVE ACTIVITY IS LOW
     EQUIVALENT WEIGHT PERCENT WATER GREATER THAN 2.5%
     XXXXX BED FAILED TEST XXXXX The criterion used by applicant (G. W. Miller) to determine whether the bed passes or fails the activity test is based on the value for the equivalent weight percent water. A bed passes the test if;
  Equivalent Weight Percent Water ≦2.5%
The rationale used by applicant (G. W. Miller) for arriving at this criterion is based on the manufacturer's as-shipped specification for water content of ≦1.5%. An additional 1% water content was allowed for water adsorption which occurs during loading of the concentrator beds. A water content of 2.5% is equivalent to a 5AMG and MG3 molecular sieve activity of 66.8% and 59.6%, respectively.

ALTERNATIVES

1. The FORTRAN program could be stored in an integrated circuit and installed inside the bed tester apparatus. This change would permit running the program independent of a personal or mainframe computer. A keyboard would have to be added to allow the user to input the needed values to the program.

2. The entire invention could be embodied in an automated system. This improvement would involve a fairly substantial modification to the existing apparatus and program. The manual valves would be replaced with solenoid actuated valves. The program would require incorporation of a data acquisition and control routine. Additional electronic circuits would be required for interfacing the pressure transducers and scale with the integrated circuits executing the program.

3. The method using the tester of FIG. 2 could also be carried out by hand without the use of a computer, using instructions, formulas and tables on paper. Of course a calculator would be used for performing the mathematical calculations. However, this method would be tedious if repeated for many tests.

It is understood that certain modifications to the invention as described may be made, as might occur to one with skill in the field of the invention, within the scope of the appended claims. Therefore, all embodiments contemplated hereunder which achieve the objects of the present invention have not been shown in complete detail. Other embodiments may be developed without departing from the scope of the appended claims. The terms "tube" and "tubing" refer broadly to any hollow conduit for conveying fluids.

APPENDIX I

```
C     BED TESTER PROGRAM (VERSION 1.0)
C     5 OCT 87
C
C     OWNER:
C     CAPT GEORGE W. MILLER
C     USAF SCHOOL OF AEROSPACE MEDICINE
C     CREW TECHNOLOGY DIVISION
C     BROOKS AFB, TEXAS 78235
C
C     NOMENCLATURE
C
C     BEDID    = BED ID NUMBER
C     ITYPE    = CONCENTRATOR TYPE
C     BEDVOL   = MOLECULAR SIEVE BULK VOLUME (ML)
C     RHOMG3   = BULK DENSITY FOR MG3 PELLETS (GM/ML)
C     RHO5AMG  = BULK DENSITY FOR 5AMG PELLETS (GM/ML)
C     VHECHAM  = VOLUME OF THE HELIUM CHAMBER (ML)
C     VBETA    = VOLUME OF THE BETA CAGES (ML)
C     ITINIHE  = INITIAL TEMP. OF THE HELIUM CHAMBER (C)
C     ITFINHE  = FINAL TEMP. OF THE HELIUM SYSTEM (C)
C     PINIHE   = INITIAL HELIUM CHAMBER PRESSURE (PSIA)
C     PFINHE   = FINAL HELIUM PRESSURE FOR SYSTEM (PSIA)
C     DELWT    = WT GAIN AFTER NITROGEN ADSORPTION (GM)
C     VTOTAL   = TOTAL SYSTEM VOLUME (ML)
C     VCONN    = VOLUME IN BED TUBING CONNECTION (ML)
C     VVOID    = VOID VOLUME OF THE MOLECULAR SIEVE BED EXCLUDING
C                BETA CAGES (ML)
C     VB13XC   = VOLUME OF BETA CAGES FOR 13X CRYSTAL (ML/GM)
C     VB5AC    = VOLUME OF BETA CAGES FOR 5A CRYSTAL (ML/GM)
C     VVOIDHE  = VOID VOLUME OF BED INCLUDING BETA CAGES (ML)
C     ITFINN2  = BED TEMPERATURE AFTER NITROGEN ADSORPTION (C)
C     PFINN2   = FINAL BED PRESSURE (PSIA)
C     XNHE     = MOLES OF HELIUM (GMOLES)
C     WTMG3    = WEIGHT OF ACTIVATED MG3 (GM)
C     WT5AMG   = WEIGHT OF ACTIVATED 5AMG (GM)
C     Q13XC    = N2 ADSORBED FOR 13X CRYSTAL (ML STP/GM)
C     Q5AC     = N2 ADSORBED FOR 5A CRYSTAL (ML STP/GM)
C     XN2GAS   = MOLES OF N2 IN THE GAS PHASE (GMOL)
C     WTN2GAS  = WT OF N2 IN THE GAS PHASE (GM)
C     IT       = ADSORPTION TEMP (C)
C     QMG3     = AMOUNT OF N2 ADSORBED FOR MG3 (ML STP/ GM)
```

```fortran
C      Q5AMG    = AMOUNT OF N2 ADSORBED FOR 5AMG (ML STP/ GM)
C      ISIEVE   = TYPE OF SIEVE
C      TIME     = TIME OF DAY
C
C
C
       DIMENSION P113XC(50),P213XC(50),P313XC(50)
       DIMENSION P15AC(50),P25AC(50),P35AC(50)
       CHARACTER*5 TIM
       CHARACTER*10 DAT
       CHARACTER*30 BEDID
       CHARACTER ESC
C
       ESC = CHAR(27)
       OPEN(1, FILE = 'TESTER.DAT', STATUS ='NEW')
C
C      DATA
C
       R = 0.0821
       VCONN = 25.82
       VHECHAM = 865.9
       RHOMG3   = 0.7164
       RHO5AMG  = 0.7458
       VB13XC   = 0.050400
       VB5AC    = 0.068206
C
       WRITE (*,10)ESC, ESC
10     FORMAT(' ',A1, 'E', A1, 'Y&&')
       WRITE (*, 12)
12     FORMAT(18X, ' ENTER DATE (ie., 07-23-1987) : '\)
       READ (*, 15) DAT
15     FORMAT(A10)
       WRITE (*, 17)
17     FORMAT(/, 18X, ' ENTER TIME (ie., 10:29) : '\)
       READ (*, 19) TIM
19     FORMAT(A5)
       WRITE(*, 20) ESC
20     FORMAT(' ', A1, 'E')
       WRITE (*,25)DAT
25     FORMAT(//, 28X, 'DATE :',A10)
       WRITE (*,30)TIM
30     FORMAT(28X, 'TIME :',A5)
       WRITE(*,40)
40     FORMAT(/,18X,'This program was written by Capt George W. Miller'/
      -18X,'USAF School of Aerospace Medicine, Crew Technology'/
      -18X,'Division, Brooks AFB, Texas, for the purpose of'/
      -18X,'determining the activity of molecular sieve inside'/
      -18X,'beds of molecular sieve oxygen concentrators. This'/
      -18X,'interactive program must be used with the BED TESTER'/
      -18X,'apparatus. At present the program will test the'/
      -18X,'following concentrators and molecular sieves:'//
      -18X,'Molecular Sieves'/
      -22X,'5AMG (Union Carbide 16x40 Mesh)'/
      -22X,'MG3  (Union Carbide 16x40 Mesh)'//
      -18X,'Concentrators'/
      -22X,'NGL 3-bed prototype (Model 2298W000)'/
      -22X,'Clifton Precision 2-bed prototype (F-16 unit)'/
      -22X,'NGL 6-bed B-1B unit'//
      -18X,'PRESS RETURN TO CONTINUE'\)
C
       READ (*, 41) RESPONSE
41     FORMAT(A1)
C
42     WRITE (*, 10) ESC, ESC
C
```

```
        WRITE(*,50)
50      FORMAT(18X, 'PLEASE CHOOSE THE TYPE OF MOLECULAR SIEVE:'///
       +       18X,'1   5AMG  (Union Carbide 16x40 Mesh)'//
       +       18X,'2   MG3   (Union Carbide 16x40 Mesh)'//
       +       18X,'3   EXIT'///
       +       18X,'  YOUR CHOICE : '\)
        READ(*,100)ISIEVE
100     FORMAT (I1)
        IF (ISIEVE .EQ. 3) GO TO 9999
        IF (ISIEVE.LT.1.OR.ISIEVE.GT.3) GO TO 42
        WRITE (*,10)ESC,ESC
C
        WRITE (*,110)
110     FORMAT(18X,'ENTER THE BED IDENTIFICATION NUMBER : '\)
        READ (*,111)BEDID
111     FORMAT(30A)
121     WRITE(*,10)ESC,ESC
C
        WRITE(*,130)
130     FORMAT(18X,'PLEASE CHOOSE CONCENTRATOR TYPE : '///
       +       18X,'    1    NGL 3-BED PROTOTYPE.'//
       +       18X,'    2    CLIFTON 2-BED PROTOTYPE '//
       +       18X,'    3    NGL B-1B UNIT'//
       +       18X,'    4    EXIT'///
       +       18X,'YOUR CHOICE : '\)
        READ (*,100) ITYPE
        IF (ITYPE.LT.1.OR.ITYPE.GT.4) GO TO 121
          IF (ITYPE.EQ.1) THEN
              BEDVOL = 4011.6
          ELSE IF (ITYPE.EQ.2) THEN
              BEDVOL = 3248.5
          ELSE IF (ITYPE.EQ.3) THEN
              BEDVOL = 2982.8
          ELSE
              GO TO 9999
          ENDIF
174     WRITE(*,10)ESC,ESC
C
C
        WRITE(*,180)
180     FORMAT(18X,'Initialize the BED TESTER apparatus:'/
       -/,18X,'PRESSURE selector:  "BED."'/
       -/,18X,'MODE selector:   "VENT."'/
       -/,18X,'HE PREP selector:  "OFF."'/
       -/,18X,'HE selector:   "OFF."'/
       -/,18X,'N2 selector:   "OFF."'/
       -/,18X,'VAC selector:  "OFF."'/
       -/,18X,'Place bed on bench and connect to the BED TESTER.'/
       -/,18X,'Do not install the temperature probe on the bed.'/
       -/,18X, 'PRESS RETURN TO CONTINUE'\)
        READ (*, 41) RESPONSE
        WRITE (*, 10) ESC, ESC
C
        WRITE(*,190)
190     FORMAT(28X,'HE selector to "ON."'/
       -/,28X,'N2 selector to "ON."'/
       -/,28X,'VAC selector to "ON."'/
       -/,28X, 'PRESS RETURN TO CONTINUE'\)
        READ (*, 41) RESPONSE
        WRITE (*,10) ESC, ESC
C
        WRITE(*,200)
200     FORMAT(18X,'Rotate PRESSURE selector CLOCKWISE to "He SUP."'/
```

```
             -/,18X, 'Ensure PRESSURE READOUT indicates 55-60 psia.'/
             -/,18X, 'PRESS RETURN TO CONTINUE'\)
             READ (*, 41) RESPONSE
             WRITE(*,10)ESC, ESC
      C
             WRITE(*,210)
      210    FORMAT(18X,'Rotate PRESSURE selector CLOCKWISE to "N2 SUP."'/
             -/,18X, 'Ensure PRESSURE READOUT indicates 55-60 psia.'/
             -/,18X, 'PRESS RETURN TO CONTINUE'\)
             READ (*, 41) RESPONSE
             WRITE(*,10)ESC, ESC
      C
             WRITE (*,220)
      220    FORMAT(18X,'Rotate PRESSURE selector CLOCKWISE to "He SYS."'/
             -/,18X, 'PRESS RETURN TO CONTINUE'\)
             READ (*,41) RESPONSE
             WRITE(*,10) ESC, ESC
      C
             WRITE (*, 230)
      230    FORMAT(18X,'Rotate HE PREP. selector CLOCKWISE to "VAC"'/
             -/,18X, 'WAIT until the PRESSURE READOUT indicates 00.1 psia.'/
             -/,18X, 'PRESS RETURN TO CONTINUE'\)
             READ (*,41) RESPONSE
             WRITE(*,10)ESC, ESC
      C
             WRITE(*,240)
      240    FORMAT(18X,'Rotate HE PREP. selector CLOCKWISE to "He."'/
             -/,18X, 'PRESS RETURN TO CONTINUE'\)
             READ (*,41) RESPONSE
             WRITE(*,10) ESC, ESC
      C
             WRITE(*,250)
      250    FORMAT(18X,'Rotate HE PREP. selector CLOCKWISE to "OFF"'/
             -/,18X, 'PRESS RETURN TO CONTINUE'\)
             READ (*, 41) RESPONSE
      C
             WRITE(*, 10) ESC, ESC
             WRITE(*,260)
      260    FORMAT(18X,'Enter the PRESSURE READOUT value (psia): '\)
             READ(*,265)PINIHE
      265    FORMAT(F5.1)
      C
             WRITE(*,270)
      270    FORMAT(//,18X,'Enter the TEMPERATURE READOUT value (C): '\)
             READ(*,271)ITINIHE
      271    FORMAT(I2)
             WRITE(*,10)ESC, ESC
      C
             WRITE(*,280)
      280    FORMAT(18X,'Rotate the PRESSURE selector CLOCKWISE to "BED".'/
             -/,18X, 'PRESS RETURN TO CONTINUE'\)
             READ (*, 41) RESPONSE
             WRITE(*,10)ESC, ESC
      C
             WRITE(*,290)
      290    FORMAT(18X,'Rotate the MODE selector //CLOCKWISE// to "VAC."'/
             -/,18X, 'WAIT until the PRESSURE READOUT indicates 01.0 psia.'/
             -/,18X, 'PRESS RETURN TO CONTINUE'\)
             READ(*, 41) RESPONSE
      C
             WRITE(*, 10) ESC, ESC
             WRITE(*,300)
      300    FORMAT(18X,'Install the temp. probe at the bed midpoint.'/
```

```
            -/,18X, 'PRESS RETURN TO CONTINUE'\)
            READ(*, 41) RESPONSE
            WRITE(*,10)ESC, ESC
C
            WRITE(*,310)
310         FORMAT(18X,'Rotate the MODE selector CLOCKWISE to "He."'/
           -/,18X, 'PRESS RETURN TO CONTINUE'\)
            READ(*, 41) RESPONSE
C
            WRITE(*, 10) ESC, ESC
            WRITE(*,320)
320         FORMAT(18X,'Enter the PRESSURE READOUT value (psia): '\)
            READ(*,265)PFINHE
C
            WRITE(*, 330)
330         FORMAT(//, 18X,'Enter the TEMPERATURE READOUT value (C): '\)
            READ(*, 271)ITFINHE
            WRITE(*,10 )ESC, ESC
C
            WRITE(*,340)
340         FORMAT(18X,'Rotate the MODE selector COUNTERCLOCKWISE to "VAC"'/
           -/,18X, 'WAIT until the PRESSURE READOUT indicates 01.0 psia'/
           -/,18X, 'PRESS RETURN TO CONTINUE'\)
            READ (*, 41) RESPONSE
            WRITE(*, 10) ESC, ESC
C
            WRITE(*,341)
341         FORMAT(18X,'Place the bed on the scale.'/
           -/,18X, 'WAIT 60 SECONDS for scale stabilization.'/
           -/,18X, 'PRESS RETURN TO CONTINUE'\)
            READ (*, 41) RESPONSE
            WRITE(*, 10) ESC, ESC
C
            WRITE(*,350)
350         FORMAT(18X,'Press the TARE switch on the scale'/
           -/,18X, 'Rotate the MODE selector COUNTERCLOCKWISE to "N2"'/
           -/,18X, 'WAIT until the PRESSURE READOUT stabilizes.'/
           -/,18X, 'PRESS RETURN TO CONTINUE'\)
            READ (*, 41) RESPONSE
C
            WRITE(*, 10) ESC, ESC
            WRITE(*,360)
360         FORMAT(18X,'Enter the PRESSURE READOUT value (psia): '\)
            READ(*,265)PFINN2
C
            WRITE(*,370)
370         FORMAT(//, 18X,'Enter the TEMPERATURE READOUT value (C): '\)
            READ(*,271)ITFINN2
C
            WRITE(*,380)
380         FORMAT(//, 18X,'Enter the WEIGHT READOUT value (g): '\)
            READ(*,265)DELWT
            WRITE(*,10)ESC, ESC
C
            WRITE(*,390)
390         FORMAT(18X,'Rotate the MODE selector COUNTERCLOCKWISE to "VENT"'/
           -/,18X, 'Rotate the HE selector to "OFF."'/
           -/,18X, 'Rotate the N2 selector to "OFF."'/
           -/,18X, 'Rotate the VAC selector to "OFF."'/
           -/,18X, 'Remove the bed from the scale.'/
           -/,18X, 'Remove and store the temperature sensor.'/
           -/,18X, 'Press TARE switch on scale.'/
           -/,18X, 'PRESS RETURN TO CONTINUE'\)
```

```
      READ (*, 41) RESPONSE
      WRITE(*, 10) ESC, ESC
C
C
C    13X:
C
      P113XC(14) = .0242349
      P213XC(14) = .000243729
      P313XC(14) = .9522
C
      P113XC(16) = .0231154
      P213XC(16) = .000242912
      P313XC(16) = .952613
C
      P113XC(18) = .0232921
      P213XC(18) = .000224263
      P313XC(18) = .942288
C
      P113XC(20) = .0204310
      P213XC(20) = .000212766
      P313XC(20) = .956809
C
      P113XC(22) = .0186361
      P213XC(22) = .000199833
      P313XC(22) = .964143
C
      P113XC(24) = .0186320
      P213XC(24) = .000191248
      P313XC(24) = .955512
C
      P113XC(26) = .0181494
      P213XC(26) = .000176
      P313XC(26) = .951013
C
      P113XC(28) = .0180745
      P213XC(28) = .000167549
      P313XC(28) = .943919
C
      P113XC(30) = .0160790
      P213XC(30) = .000162011
      P313XC(30) = .956375
C
      P113XC(32) = 0.0156924
      P213XC(32) = 0.000150793
      P313XC(32) = 0.953257
C
      P113XC(34) = 0.0145200
      P213XC(34) = 0.000134640
      P313XC(34) = 0.955181
C
      P113XC(36) = 0.0152611
      P213XC(36) = 0.000137591
      P313XC(36) = 0.945010
C
      P113XC(38) = 0.0166012
      P213XC(38) = 0.000142447
      P313XC(38) = 0.926577
C
      P113XC(40) = 0.0156244
      P213XC(40) = 0.000136537
      P313XC(40) = 0.931126
C
      P113XC(42) = 0.0103943
      P213XC(42) = 0.000128056
      P313XC(42) = 0.987436
```

```
C       P113XC(44) = 0.0110950
        P213XC(44) = 0.000116631
        P313XC(44) = 0.969449
C
C       5A:
C
        P15AC(14)= .0466579
        P25AC(14)= .000515761
        P35AC(14)= .904132
C
        P15AC(16)= .0502004
        P25AC(16)= .000517713
        P35AC(16)= .882407
C
        P15AC(18)= .0440647
        P25AC(18)= .000478184
        P35AC(19)= .894204
C
        P15AC(20)= .0383118
        P25AC(20)= .000420350
        P35AC(20)= .905389
C
        P15AC(22)= .0404727
        P25AC(22)= .000426228
        P35AC(22)= .889692
C
        P15AC(24)= .0354915
        P25AC(24)= .000392717
        P35AC(24)= .902795
C
        P15AC(26)= .0282781
        P25AC(26)= .000334384
        P35AC(26)= .929083
C
        P15AC(28)= .0325641
        P25AC(28)= .000347735
        P35AC(28)= .899242
C
        P15AC(30)= .0296863
        P25AC(30)= .000328863
        P35AC(30)= .906961
C
        P15AC(32)= 0.0181812
        P25AC(32)= 0.000224080
        P35AC(32)= 0.970922
C
        P15AC(34)= 0.0160255
        P25AC(34)= 0.000198171
        P35AC(34)= 0.978388
C
        P15AC(36)= 0.0223386
        P25AC(36)= 0.000220271
        P35AC(36)= 0.920666
C
        P15AC(38)= 0.0156755
        P25AC(38)= 0.000184893
        P35AC(38)= 0.966943
C
        P15AC(40)= 0.0178641
        P25AC(40)= 0.000193876
        P35AC(40)= 0.941110
C
```

```
            P15AC(42)= 0.0168994
            P25AC(42)= 0.000178651
            P35AC(42)= 0.940574
C
            P15AC(44)= 0.0116883
            P25AC(44)= 0.000161842
            P35AC(44)= 0.991612
C
C           CALCULATIONS
C
C
            IT = ITFINN2
            IF (IT.LT.14 .OR. IT.GT.44) GO TO 415
C
C           16x40 Mesh 5AMG:
C
            IF (ISIEVE.EQ.2) GO TO 1000
400         WT5AMG = BEDVOL * RHO5AMG
            XPINIHEX = PINIHE / 14.7
            XPFINHEX = PFINHE / 14.7
            TINIHE = ITINIHE + 273.15
            TFINHE = ITFINHE + 273.15
            VHECHAM = VHECHAM / 1000.
            VCONN = VCONN / 1000.
            XNHE = (XPINIHEX * VHECHAM) / (R * TINIHE)
            VTOTAL = (XNHE * R * TFINHE) / XPFINHEX
            VVOIDHE = VTOTAL - VHECHAM - VCONN
            VBETA = (WT5AMG * .3 * VB5AC) / 1000.
            VVOID = VVOIDHE - VBETA
C
            ICK = 14
            DO410 I=1,16
            IF (IT.EQ.ICK) GO TO 411
            ICK = ICK + 2
410         CONTINUE
C
            DO 412 I = 14, 44
            IA = I
            IB = I + 2
            ITEST1 = IT - IA
            ITEST2 = IB - IT
            IF (ITEST1.EQ.ITEST2) GO TO 413
412         CONTINUE
413         TPFINN2T = (PFINN2 / 14.7) * 760.
            X = TPFINN2T**P35AC(IA)
            Q5ACA = (P15AC(IA) * X) / (1.0 + P25AC(IA)*X)
            Y = TPFINN2T**P35AC(IB)
            Q5ACB = (P15AC(IB) * Y) / (1.0 + P25AC(IB)*Y)
            Q5AC = (Q5ACA + Q5ACB) / 2.0
            GO TO 420
411         TPFINN2T = (PFINN2 / 14.7) * 760.
            Z = TPFINN2T**P35AC(IT)
            Q5AC = (P15AC(IT)*Z) / (1.0 + P25AC(IT)*Z)
C
C
420         XPFINN2X = PFINN2 / 14.7
            TFINN2 = ITFINN2 + 273.15
            XNN2GAS = (XPFINN2X * VVOID) / (R * TFINN2)
            WTN2GAS = XNN2GAS * 28.0134
            DELWT = DELWT - WTN2GAS
            XNN2ADS = DELWT / 28.0134
            Q5AMG = (XNN2ADS * R * 273.15) * 1000.
C
```

```
      QMAX = Q5AC * WT5AMG * .8
      ACT = (Q5AMG / QMAX) * 100.
      WATER = -1.96215 + 23.338246889*EXP(-0.024760528*ACT)
      GO TO 2000
C
C
C     16X40 MESH MG3
C
1000  WTMG3 = BEDVOL * RHOMG3
      XPINIHEX = PINIHE / 14.7
      XPFINHEX = PFINHE / 14.7
      TINIHE = ITINIHE + 273.15
      TFINHE = ITFINHE + 273.15
      VHECHAM = VHECHAM / 1000.
      VCONN = VCONN / 1000.
      XNHE = (XPINIHEX * VHECHAM) / (R * TINIHE)
      VTOTAL = (XNHE * R * TFINHE) / XPFINHEX
      VVOIDHE = VTOTAL - VHECHAM - VCONN
      VBETA = (WTMG3 * .8 * VB13XC) / 1000.
      VVOID = VVOIDHE - VBETA
C
      ICK = 14
      DO 910 I = 1, 16
      IF (IT.EQ.ICK) GO TO 911
      ICK = ICK + 2
910   CONTINUE
C
      DO 912 I = 14, 44
      IA = I
      IB = I + 2
      ITEST1 = IT - IA
      ITEST2 = IB - IT
      IF (ITEST1.EQ.ITEST2) GO TO 913
912   CONTINUE
913   TPFINN2T = (PFINN2 / 14.7) * 760.
      X = TPFINN2T**P313XC(IA)
      Q13XCA = (P113XC(IA) * X) / (1.0 + P213XC(IA)*X)
      Y = TPFINN2T**P313XC(IB)
      Q13XCB = (P113XC(IB) * Y) / (1.0 + P213XC(IB)*Y)
      Q13XC = (Q13XCA + Q13XCB) / 2.0
      GO TO 920
911   TPFINN2T = (PFINN2 / 14.7) * 760.
      Z = TPFINN2T**P313XC(IT)
      Q13XC = (P113XC(IT)*Z) / (1.0 + P213XC(IT)*Z)
C
C
920   XPFINN2X = PFINN2 / 14.7
      TFINN2 = ITFINN2 + 273.15
      XNN2GAS = (XPFINN2X * VVOID) / (R * TFINN2)
      WTN2GAS = XNN2GAS * 28.0134
      DELWT = DELWT - WTN2GAS
      XNN2ADS = DELWT / 28.0134
      QMG3 = (XNN2ADS * R * 273.15) * 1000.
      QMAX = Q13XC * WTMG3 * .8
      ACT = (QMG3 / QMAX) * 100.
      WATER = -0.7140699 + 29.679412844*EXP(-0.03727228*ACT)
      GO TO 2000
C
C
C     DISPLAY RESULTS
C
415   IRANGE = 1
2000  WRITE(*, 10) ESC,ESC
      WRITE(1,2010)DAT
2010  FORMAT(/,10X, 'DATE: ',A10)
```

```
            WRITE(1,2020)TIM
2020    FORMAT(10X,'TIME: ',A5)
C
        WRITE(*,2030)BEDID
        WRITE(1,2030)BEDID
2030    FORMAT(/,10X,'BED IDENTIFICATION NO.:   ',30A)
C
        IF (ITYPE.EQ.1) THEN
            GO TO 2031
        ELSE IF (ITYPE.EQ.2) THEN
            GO TO 2032
        ELSE
            GO TO 2035
        ENDIF
2031    WRITE(*,2033)
        WRITE(1,2033)
2033    FORMAT(10X,'CONCENTRATOR TYPE:   NGL 3-BED PROTOTYPE')
        GO TO 2040
2032    WRITE(*,2034)
        WRITE(1,2034)
2034    FORMAT(10X,'CONCENTRATOR TYPE:   CLIFTON 2-BED PROTOTYPE')
        GO TO 2040
2035    WRITE(*,2036)
        WRITE(1,2036)
2036    FORMAT(10X,'CONCENTRATOR TYPE:   NGL B-1B UNIT')
2040    IF (ISIEVE.EQ.1) GO TO 2041
        IF (ISIEVE.EQ.2) GO TO 2042
2041    WRITE(*,2043)
        WRITE(1,2043)
2043    FORMAT(10X,'TYPE OF MOLECULAR SIEVE:  U. C. 16X40 MESH 5AMG')
        GO TO 2050
2042    WRITE(*,2044)
        WRITE(1,2044)
2044    FORMAT(10X,'TYPE OF MOLECULAR SIEVE:  U. C. 16X40 MESH MG3')
C
2050    WRITE(*,2070)
        WRITE(1,2070)
2070    FORMAT(/,10X,'INPUT PARAMETERS:')
        WRITE(*,2045)PINIHE
        WRITE(1,2045)PINIHE
2045    FORMAT(10X,'INITIAL HELIUM PRESSURE (psia) = ',F5.1)
        WRITE(*,2046)ITINIHE
        WRITE(1,2046)ITINIHE
2046    FORMAT(10X,'INITIAL HELIUM TEMPERATURE (C) = ',I2)
        WRITE(*,2047)PFINHE
        WRITE(1,2047)PFINHE
2047    FORMAT(10X,'FINAL HELIUM PRESSURE (psia) = ',F5.1)
        WRITE(*,2048)ITFINHE
        WRITE(1,2048)ITFINHE
2048    FORMAT(10X,'FINAL HELIUM TEMPERATURE (C) = ',I2)
        WRITE(*,2049)PFINN2
        WRITE(1,2049)PFINN2
2049    FORMAT(10X,'FINAL BED PRESSURE (psia) = ',F5.1)
        WRITE(*,2052)ITFINN2
        WRITE(1,2052)ITFINN2
2052    FORMAT(10X,'FINAL BED TEMPERATURE (C) = ',I2)
        DELWT = DELWT + WTN2GAS
        WRITE(1,2053)DELWT
        WRITE(*,2053)DELWT
2053    FORMAT(10X,'WEIGHT GAIN (g) = ',F5.1)
        IF(IRANGE.EQ.1) GO TO 3000
C
        WRITE(*,8011)
        WRITE(1,8011)
```

```
8011  FORMAT(/,10X,'RESULTS:')
      WRITE(*,2051)ACT
      WRITE(1,2051)ACT
2051  FORMAT(10X,'BED ACTIVITY   =  ',F10.1,' % ')
C
      WRITE(*,8010)WATER
      WRITE(1,8010)WATER
8010  FORMAT(10X,'EQUIVALENT WEIGHT % WATER  =   ',F10.2,' % ')
      IF(WATER.GT.2.5) GO TO 2075
      WRITE(*,2081)
      WRITE(1,2081)
2081  FORMAT(/,10X,'MOLECULAR SIEVE ACTIVITY IS ACCEPTABLE ')
      WRITE(*,4111)
      WRITE(1,4111)
4111  FORMAT(10X,'EQUIVALENT WEIGHT % WATER LESS THAN OR EQUAL TO',
     +       ' 2.5%')
      WRITE(*,4000)
      WRITE(1,4000)
4000  FORMAT(10X,'/////  BED PASSED TEST  /////')
      GO TO 9999
C
2075  WRITE(*,2076)
      WRITE(1,2076)
2076  FORMAT(/,10X,'MOLECULAR SIEVE ACTIVITY IS LOW ')
      WRITE(*,4112)
      WRITE(*,4112)
4112  FORMAT(10X,'EQUIVALENT WEIGHT % WATER GREATER THAN 2.5%')
      WRITE(*,2077)
      WRITE(1,2077)
2077  FORMAT(10X,'XXXXX  BED FAILED TEST  XXXXX')
      GO TO 9999
C
3000  WRITE(*,414)
414   FORMAT(/,18X,'FINAL TEMPERATURE IS OUTSIDE RANGE OF PROGRAM'
     -//,25X, 'UNABLE TO COMPUTE RESULTS',/)
C
9999  STOP
      END
```

APPENDIX II

```
DATE: 01-11-1988
TIME: 10:31

BED IDENTIFICATION NO.:   2341234
CONCENTRATOR TYPE:   NGL 3-BED PROTOTYPE
TYPE OF MOLECULAR SIEVE:   U. C. 16X40 MESH 5AMG

INPUT PARAMETERS:
INITIAL HELIUM PRESSURE (psia) =  60.1
INITIAL HELIUM TEMPERATURE (C) = 24
FINAL HELIUM PRESSURE (psia) = 13.4
FINAL HELIUM TEMPERATURE (C) = 24
FINAL BED PRESSURE (psia) =  60.3
FINAL BED TEMPERATURE (C) = 31
WEIGHT GAIN (g) =  80.4

RESULTS:
BED ACTIVITY =           77.2 %
EQUIVALENT WEIGHT % WATER  =       1.49 %

MOLECULAR SIEVE ACTIVITY IS ACCEPTABLE
EQUIVALENT WEIGHT % WATER LESS THAN OR EQUAL TO 2.5%
/////  BED PASSED TEST  /////
```

What is claimed is:

1. A bed tester for testing a bed of molecular sieve oxygen concentrator for determining activity, said bed having molecular sieve pellets with beta cages for adsorption of nitrogen, comprising:

bed test apparatus which comprises a helium system with a chamber of known volume, weighing means for measuring the weight gain of the bed due to nitrogen adsorption, pressure measuring means for measuring the pressure in the helium system and in the bed, temperature measuring means for measuring the temperature in the helium system and in the bed;

valve means having positions for selectively connecting the helium system to a vacuum source, for connecting the helium system to a source of helium under pressure, for connecting the helium system to the bed, for connecting the bed to the vacuum source, and for connecting the bed to a source of nitrogen under pressure;

so that the helium system may be filled with helium and the pressure and temperature measured, the helium system may be connected to the bed for the helium to expand and the pressure and temperature measured, and the bed may be evacuated and weighed and then pressurized with nitrogen, and the pressure and temperature measured, and the bed weighed.

2. A bed tester according to claim 1, which further includes a computer program which includes:

means for entering the measured initial values of pressure and temperature in the helium system filled with helium, final values of pressure and temperature of the helium after expansion into the bed, values of nitrogen pressure and temperature after the bed is pressurized with nitrogen, and a value of weight gain after the bed is pressurized with nitrogen;

means for calculating the weight $Q_X$ of nitrogen adsorbed for the bed under test, using said values of pressure, temperature and weight gain, and values of volume and density from a table, using the ideal gas law (PV=MRT) and other equations in calculations to arrive at the true weight gain due to nitrogen adsorption;

means for determining the weight $Q_M$ of nitrogen adsorbed by an equivalent weight of activated molecule sieve using a set of pure crystal isotherm parameters, which are stored in a table and were determined by collecting pure crystal-N2 isotherm data for the zeolite crystals over a given temperature range and fit to a Sips equation by a least squares technique;

means for calculating the activity as the ratio of the weight of nitrogen adsorbed in the bed under test to the weight of nitrogen adsorbed by an equivalent weight of activated molecular sieve ($Q_X/Q_M$).

3. A bed tester according to claim 2, wherein said computer program further includes means for calculating the weight percent of water of the molecular sieve based on correlations with activity determined by a least squares technique.

4. A bed tester according to claim 2, wherein said means comprising said computer program include equations as follows:

$$W_x = V_b \cdot \rho$$

$$P_{hi} = P_{hia}/14.7$$

$$P_{hf} = P_{hfa}/14.7$$

$$T_{hi} = T_{hia} + 273.15$$

$$T_{hf} = T_{hfa} + 273.15$$

$$V_{hi} = V_{hia}/1000$$

$$V_c = V_{ca}/1000$$

$$M_h = (P_{hi} \cdot V_{hi})/(R \cdot T_{hi})$$

$$V_t = (M_h \cdot R \cdot T_{hf})/P_{hf}$$

$$V_{vh} = V_t - V_{hi} - V_c$$

$$V_\beta = (W_x \cdot 0.8 \cdot V_x)/1000$$

$$V_v = V_{vh} - V_\beta$$

$$Q_n = (a \cdot P_n^c)/(1 + b \cdot P_n^c)$$

$$P_n = (P_{na}/14.7) \cdot 760$$

$$T_n = T + 273.15$$

$$M_n = (P_{nb} \cdot V_v)/(R \cdot T_n)$$

$$W_n = M_n \cdot 28.0134$$

$$\Delta W_b = \Delta W_a - W_n$$

$$\Delta W = \Delta W_b/28.0134$$

$$Q_X = (\Delta W \cdot R \cdot 273.15) \cdot 1000$$

$$Q_M = Q_n \cdot W_x \cdot 0.8$$

$$X = (Q_X/Q_M) \cdot 100$$

the nomeclature in the above equations being as follows with the units in the last column:

| | | |
|---|---|---|
| $P_{hia}$ | Initial helium system pressure | psia |
| $P_{hi}$ | " | atm |
| $P_{hfa}$ | Final helium system pressure | psia |
| $P_{hf}$ | " | atm |
| $P_{ha}$ | Final bed pressure with N2 | psia |
| $P_{nb}$ | " | atm |
| $P_n$ | " | torr |
| $T_{hia}$ | Initial helium system temperature | C |
| $T_{hi}$ | " | K |
| $T_{hfa}$ | Final helium system temperature | C |
| $T_{hf}$ | " | K |
| $T$ | Final bed temperature with N2 | C |
| $T_n$ | " | K |
| $V_b$ | Molecular sieve bulk volume | ml |
| $V_{hia}$ | Helium plenum volume | ml |
| $V_{hi}$ | " | liter |
| $V_{ca}$ | Bed tubing volume | ml |
| $V_c$ | " | liter |
| $V_{vh}$ | Void volume of bed including $\beta$-cages | liter |
| $V_\beta$ | Volume of $\beta$-cages | liter |
| $V_v$ | Void volume of bed excluding $\beta$-cages | liter |
| $V_x$ | Void volume of $\beta$-cages | ml/gm |
| $V_t$ | Total void volume of system | liter |
| $W_x$ | Weight of activated of molecular sieve | gm |
| $W_n$ | Weight of N2 in gas phase | gm |
| $M_n$ | Moles of N2 in gas phase | moles |
| $\Delta W_a$ | Weight gain after N2 adsorption | gm |
| $\Delta W_b$ | True weight gain due to N2 adsorption | gm |
| $\Delta W$ | " | moles |
| $M_h$ | Moles of helium | moles |
| $Q_n$ | Amount of N2 adsorbed in crystal | ml STP/gm |
| $Q_X$ | Amount of N2 adsorbed in bed | ml STP |
| $Q_M$ | Amount of N2 adsorbed by an equivalent wt. of activated molecular sieve | ml STP |
| a, b & c. Parameters from Sips equation | | |
| $\rho$ | Bulk density of pellets | gm/ml |
| R | Gas constant | atm. liter mole °K |
| X | Activity | percent |

5. A bed tester according to claim 4, wherein said computer program further includes a list of molecular sieve types which includes type MG3 and type 5AMG, means for selecting one of these types, the values from the table for void volume of $\beta$-cages ($V_x$), bulk density of pellets ($\rho$), and the parameters (a, b and c) from a Sips equation being functions of the molecular sieve type;

means for calculating the weight percent of water (Y) of the molecular sieve based on correlations with said activity (X) by executing the equation $$Y = -1.96215 + 23.338246889 \cdot e(-0.024760528 \cdot X)$$

if the selected type of molecular sieve is type 5AMG, and alternatively executing the equation $$Y = -0.7140699 + 29.679412844 \cdot e(-0.037272280 \cdot X)$$

if the selected type of molecular sieve is type MG3.

6. A bed tester according to claim 1, wherein said pressure measuring means comprises a pressure sensor electrically coupled to a pressure readout unit;

said temperature measuring means comprises a temperature sensor electrically coupled to a temperature readout unit;

said valve means comprises a first valve having a "He SUP." position connecting the pressure sensor to the source of helium, a "N2SUP." position connecting the pressure sensor to the source of nitrogen, a "He SYS." position connecting the pressure sensor to the helium system and a "BED" position connecting the pressure sensor to the bed;

a second valve having a "N2" position connecting the bed to the source of nitrogen, a "VAC." position connecting the bed to the vacuum source, a "He" position connecting the bed to the helium system, and a "VENT" position connecting the bed to a vent;

a third valve having a "Vac." position connecting the helium system to the vacuum source, a "He" position connecting the helium system to the source of helium, and an "OFF" position closing off the helium system from the vacuum source and the source of helium;

and fourth, fifth and sixth valves which are ON-OFF valves for the source of helium, the source of nitrogen, and the vacuum source respectively; and said weighing means is a scale on which the bed is placed.

7. A bed tester according to claim 6, which further includes a computer, a keyboard coupled to the computer for entries by a user, and a program for loading in the computer, said program having references to data in table and instructions for interacting with the user and for performing calculations;

instruction means having a first list of molecular sieve types and a second list of concentrator types, directions to the user to select a type from each list, and means for entering the type of each from responses at the keyboard;

wherein the data in tables includes values for the universal gas constant R, a volume $V_c$ of connecting tubing to the bed, a volume $V_{hi}$ for the helium system, bulk densities $\rho$ for pellets and volumes $V_\chi$ for beta cages for the types of molecular sieve on the first list, bed volumes $V_b$ for the types of concentrators on the second list;

wherein the data in the tables further includes values of pure crystal isotherm parameters, which were determined by collecting pure crystal nitrogen isotherm data over a given temperature range for the types of molecular sieve on the first list, then fit by a least squares technique to a Sips equation $$q = \frac{ap^c}{1 + bp^c}$$

where,
q = amount adsorbed
p = pressure
a, b, and c = parameters determined by least squares analysis and stored in the table;

instruction means for initializing the bed tester apparatus, directing the user to operate the first valve to the "BED" position, the second valve to the "VENT" position, the third valve to the "OFF" position, the fourth, fifth and sixth valves to OFF positions, to place the bed on the scale and to connect it to the bed tester, and to not install the temperature sensor on the bed;

instruction means directing the user to operate the fourth, fifth and sixth valves to ON positions;

instruction means directing the user to operate the first valve to the "He SUP." position and the "N2 SUP." in turn, and to verify that the pressure readout at each position is within stated limits;

instruction means directing the user to operate the first valve to the "He SYS." position and the third valve to the "VAC" position and to wait until the pressure readout indicates a stated value (vacuum pressure);

instruction means directing the user to operate the third valve to the "He" position (which pressurizes the hellium system from the source of helium);

instruction means directing the user to operate the third valve to the "OFF" position.

instruction means directing the user to enter the pressure readout and the temperature readout values and to enter them in turn, and means for entering these values from responses at the keyboard as an initial helium system pressure $P_{hia}$ in psia and an initial helium system temperture $T_{hia}$ in degrees C.;

instruction means directing the user to operate the first valve to the "BED" position and the third valve to the "VAC" position and to wait until the pressure readout indicates a stated value (vacuum pressure);

instruction means directing the user to install the temperature sensor at the bed midpoint;

instruction means directing the user to operate the second valve to the "He" position (which permits the helium to expand into the bed);

instruction means directing the user to enter the pressure readout and the temperature readout values and to enter them in turn, and means for entering these values from responses at the keyboard as a final helium system pressure $P_{hfa}$ in psia and a final helium system temperature $T_{hfa}$ in degrees C.;

instruction means directing the user to operate the second valve to the "VAC" position and to wait until the pressure readout indicates a stated value (vacuum pressure);

instruction means directing the user to place the bed on the scale and to press a tare switch;

instruction means directing the user to operate the second valve to the "N2" position (which pressurizes the bed with nitrogen from the source of nitrogen);

instruction means directing the user to enter the pressure readout and the temperature readout values and to enter them in turn, and means for entering these values from responses at the keyboard as a final bed pressure $P_{na}$ in psia and a final bed temperature T in degrees C;

instruction means directing the user to enter the weight indicated on the scale, and means for entering this value from a response at the keyboard as a weight gain $\Delta W_a$ in grams after nitrogen adsorption;

instruction means for shutting down the bed tester apparatus, directing the user to operate second valve to the "VENT" position, the fourth, fifth and sixth valves to OFF positions, to remove the bed from the scale, to remove and store the temperature sensor, and to press the tare switch;

instruction means for calculating the weight $W_x$ of activated molecular sieve as the product ($W_x = V_b \cdot \rho$) of the bed volume $V_b$ for the selected type of concentrator on the second list and the bulk density $\rho$ for pellets of the selected type of molecular sieve on the first list;

instruction means for executing the equations $P_{hi} = P_{hia}/14.7$, $P_{hf} = P_{hfa}/14.7$, $T_{hi} = T_{hia} + 273.15$, $T_{hf} = T_{hfa} + 273.15$, $V_{hi} = V_{hia}/1000$, $V_c = V_{ca}/1000$, $P_n = (P_{na}/14.7) \cdot 760$ and $T_n = T + 273.15$ to convert pressure values to atmospheres, temperature values to degrees Kelvin, and volume values to liters;
instruction means for executing the equation $$M_h = (P_{hi} \cdot V_{hi})/(R \cdot T_{hi})$$

using the ideal gas law to calculate the moles $M_n$ of helium in the gas phase;
instruction means for executing the equation $$V_t = (M_h \cdot R \cdot T_{hf})/P_{hf}$$

using the ideal gas law to calculate the total system volume $V_t$;
instruction means for executing the equation $$V_{vh} = V_t - V_{hi} - V_c$$

to calculate the void volume $V_{vh}$ of the bed including the beta cages;
instruction means for executing the equation $$V_\beta = (W_x \cdot 0.8 \cdot V_x)/1000$$

to calculate the volume $V_\beta$ of the beta cages;
instruction means for executing the equation $$V_v = V_{vh} - V_\beta$$

to calculate the void volume $V_v$ of the bed excluding the beta cages;
instruction means for reading the pure crystal isotherm parameters (a, b and c) from the table, interpolating if the final bed temperature with $T_n$ is between values in the table, and using these parameters in the Sips equation $$Q_n = (a \cdot P_n{}^c)/(1 + b \cdot P_n{}^c)$$

to calculate the amount $Q_n$ of nitrogen adsorbed
instruction means for executing the equations $$M_n = (P_{nb} \cdot V_v)/(R \cdot T_n)$$

and $$W_n = M_n \cdot 28.0134$$

using the ideal gas law to calculate the moles $M_n$ of nitrogen in the gas phase and the corresponding weight $W_n$ in grams;
instruction means for executing the equations $$\Delta W_b = \Delta W_a - W_n$$

$$\Delta W = \Delta W_b / 28.0134$$

$$Q_x = (\Delta W \cdot R \cdot 273.15) \cdot 1000$$

to calculate the true weight gain due to nitrogen adsorption first in grams ($\Delta W_b$), converting to moles ($\Delta W$), then to ml at standard temperature and pressure;
instruction means for executing the equation $$Q_M = Q_n \cdot W_x \cdot 0.8$$

to calculate the amount of nitrogen in ml per gram at standard temperature and pressure, corrected to account for a twenty weight percent binder content of the molecular sieve pellets; and
instruction means for executing the equation $$X = (Q_X/Q_M) \cdot 100$$

to calculate the activity (X) in the bed in percent.

8. A bed tester according to claim 7, wherein said first list of molecular sieve types includes 16×40 mesh type MG3 and type 5AMG;
wherein said program further includes instruction means for calculating the weight percent water (Y) of the molecular sieve by executing the equation $$Y = -1.9621500 + 23.338246889 * \text{EXP}(-0.024760528 * X)$$

if the selected type of molecular sieve is type 5AMG, and alternatively executing the equation $$Y = -0.7140699 \pm 29.679412844 * \text{EXP}(-0.037272280 * X)$$

if the selected type of molecular sieve is type MG3.

9. The method of testing a bed of a molecular sieve oxygen concentrator for determining activity, said bed having molecular sieve pellets for adsorption of nitrogen, said method comprising the steps:
filling a chamber having a known volume $V_{hi}$ with helium, measuring the initial helium pressure $P_{hi}$ and temperature $T_{hi}$, and employing the ideal gas law to calculate the mass of the helium $M_h$, using a value for the universal gas constant R from a table, as $$M_h = (P_{hi} \cdot V_{hi})/(R \cdot T_{hi});$$

connecting the chamber to the evacuated bed and allowing the helium to expand into the bed, measuring the final helium pressure $P_{hf}$ and temperature $T_{hf}$ in the bed, and employing the ideal gas law to calculate the total void volume $V_t$ of the bed and chamber, based on the mass of the helium $M_h$, as $$V_t = (M_h \cdot R \cdot T_{hf})/P_{hf};$$

determining a void volume $V_{vh}$ of the bed by subtracting the chamber volume $V_{hi}$ and a tester connection tubing volume $V_c$ from the total void volume $V_t$;
calculating the cumulative volume $V_\beta$ of the molecular sieve beta cages based on a parameter $V_x$ from a table for the void volume of the beta cages for the crystal type, and calculating a corrected void volume $V_v$ for adsorption by subtracting the volume $V_\beta$ of the beta cages from the void volume $V_{vh}$ of the bed;
removing the helium from the bed;
weighing the bed to determine a tare value;
pressurizing the bed with nitrogen;
measuring the final pressure $P_{na}$ and temperature T for the bed filled with nitrogen;
weighing the bed for the weight gain $\Delta W_a$ of the bed after pressurization with nitrogen;
calculating the amount of nitrogen $Q_n$ adsorbed per unit weight of pure crystal based on a Sips equation $$q = \frac{ap^c}{1 + bp^c}$$

where, q=amount adsorbed, p=pressure, and a, b, and c are pure crystal isotherm parameters from a table, which were determined by collecting pure crystal nitrogen isotherm data for the crystals over a given temperature range, then fit by a least squares technique to said Sips equation;

calculating the weight $W_n$ of nitrogen gas filling the bed void volume based on the final pressure $P_{nb}$ and temperature $T_n$ for the bed filled with nitrogen, the corrected void volume $V_v$, and the molecular weight of nitrogen, using the ideal gas law in the form $$W_n = ((P_{nb} \cdot V_v)/(R \cdot T_n)) \cdot 28.0134$$

calculating the true weight gain $\Delta W_b$ of the bed due to nitrogen adsorption during pressurization by subtracting the weight $W_n$ of nitrogen gas filling the bed void volume from the weight gain $\Delta W_a$ of the bed after pressurization with nitrogen, and then dividing the result by the molecular weight of nitrogen to obtain the weight gain $\Delta W$ in moles;

calculating the total amount of nitrogen $Q_X$ adsorbed by the bed, based on said weight gain $\Delta W$ in moles, using the ideal gas law in the form $$Q_X = (\Delta W \cdot R \cdot 273.15) \cdot 1000$$

calculating the total amount of nitrogen $Q_M$ adsorbed for an identical weight of activated molecular sieve, as the product of the weight $W_x$ of molecular sieve pellets within the bed and the amount of nitrogen $Q_n$ adsorbed per unit weight of pure crystal, corrected to account for a twenty weight percent binder content of the molecular sieve pellets, $$Q_M = Q_n \cdot W_x \cdot 0.8$$

calculating an activity parameter X of the molecular sieve in the bed under test by dividing the total amount of nitrogen $Q_M$ adsorbed for an identical weight of activated molecular sieve into the total amount of nitrogen $Q_X$ adsorbed by the bed $(X = (Q_X/Q_M) \cdot 100)$.

10. The method according to claim 9, which further includes the step of calculating the weight percent of water of the molecular sieve based on correlations with activity determined by a least squares technique.

11. The method of testing a bed of a molecular sieve oxygen concentrator for determining activity, using a bed tester having a plurality of valves and tubing connected to a helium source, a nitrogen source, a vacuum source, a helium chamber, a pressure sensor, and a temperature sensor, said method comprising the steps:

providing tables containing values for the universal gas constant R, a volume $V_c$ of connecting tubing to the bed, a volume $V_{hi}$ for the helium chamber, bulk densities $\rho$ for pellets of a number of types of molecular sieve crystal, volumes $V_\chi$ for beta cages for the types of molecular sieve crystal, bed volumes $V_b$ for a number of concentrator types;

providing a table of pure crystal isotherm parameters, which were determined by collecting pure crystal nitrogen isotherm data for the types of crystals over the a given temperature range, then fit by a least squares technique to a Sips equation $$q = \frac{ap^c}{1 + bp^c}$$

where,
q=amount adsorbed
p=pressure
a, b, and c=parameters determined by least aquares analysis and stored in the table;
selecting a type of molecular sieve from a list;
choosing a type of concentrator from a list;
assigning a value for a bed volume parameter $V_b$ selected from a table based on the type of concentrator chosen, $V_b$ being the volume occupied by molecular sieve pellets within the bed;
initializing the bed tester;
connecting the bed tester to the bed;
checking the pressure of the helium source;
checking the pressure of the nitrogen source;
evacuating the helium chamber to a pressure of at most 0.1 psia;
filling the helium chamber from the helium source to a pressure between 55–60 psia and then closing the connection between the helium chamber and the helium source;
measuring and entering the initial helium pressure $P_{hi}$;
measuring and entering the initial helium temperature $T_{hi}$;
evacuating the bed under test is to a pressure of at most 1.0 psia;
connecting the helium chamber to the bed and allowing the helium to expand into the bed;
measuring and entering the final helium pressure $P_{hf}$;
measuring and entering the final helium temperature $T_{hf}$ in the bed;
removing the helium from the bed;
weighing the bed to determine a tare value;
connecting the bed to the nitrogen source so that the previously evacuated bed is pressurized with nitrogen to 55–60 psia;
measuring and entering the final pressure $P_n$ for the bed filled with nitrogen;
measuring and entering the final temperature $T_n$ for the bed filled with nitrogen;
weighing the bed and entering the weight gain $\Delta W_a$ of the bed after pressurization with nitrogen;
shutting down the bed tester;
calculating the weight $W_x$ of molecular sieve pellets within the bed based on the bulk densities from a table for the molecular sieve type and the bed volume parameter $V_b$;
calculating the total void volume $V_t$ of the bed and helium chamber, based on the initial and final helium pressures $P_{hi}$ and $P_{hf}$, and the initial and final helium temperatures $T_{hi}$ and $T_{hf}$, employing the ideal gas law to first calculate the mass of the helium $M_h$ and then the total void volume $V_t$, using the equations $$M_h = (P_{hi} \cdot V_{hi})/(R \cdot T_{hi})$$

$$V_t = (M_h \cdot R \cdot T_{hf})/P_{hf}$$

determining a void volume $V_{vh}$ of the bed is by subtracting values from the table for the helium chamber volume $V_{hi}$ and a tester connection hose volume $V_c$ from the total void volume $V_t$;

calculating the cumulative volume $V_\beta$ of the molecular sieve beta cages based on the parameter $V_\chi$ from the tables for the void volume of the beta cages for the selected crystal type, and calculating a corrected void volume $V_v$ for adsorption by subtracting the volume $V_\beta$ of the beta cages from the void volume $V_{vh}$ of the bed;

calculating the amount of nitrogen $Q_n$ adsorbed per unit weight of pure crystal for the selected molecular sieve type based on said Sips equation using said parameters a, b and c from said table of pure crystal isotherm parameters for said final temperature $T_n$ for the bed filled with nitrogen;

calculating the weight $W_n$ of nitrogen gas filling the bed void volume based on the final pressure $P_{nb\,l}$ and final temperature $T_n$ for the bed filled with nitrogen, the corrected void volume $V_v$, and the molecular weight of nitrogen, using the ideal gas law in the form $$W_n = ((P_{nb}.V_v)/(R.T_n)).28.0134$$

calculating the true weight gain $\Delta W_b$ of the bed due to nitrogen adsorption during pressurization by subtracting the weight $W_n$ of nitrogen gas filling the bed void volume from the weight gain $\Delta W_a$ of the bed after pressurization with nitrogen, and then dividing the result by the molecular weight of nitrogen to obtain the weight gain $\Delta W$ in moles;

calculating the total amount of nitrogen $Q_X$ adsorbed by the bed in ml at standard temperature and pressure, based on said weight gain $\Delta W$ in moles, using the ideal gas law in the form $$Q_X = (\Delta W.R.273.15).1000$$

calculating the total amount of nitrogen $Q_M$ adsorbed for an identical weight of activated molecular sieve, as the product of the weight $W_x$ of molecular sieve pellets within the bed and the amount of nitrogen $Q_n$ adsorbed per unit weight of pure crystal, corrected to account for a twenty weight percent binder content of the molecular sieve pellets, $$Q_M = Q_n.W_x.0.8$$

calculating an activity parameter X of the molecular sieve in the bed under test by dividing the total amount of nitrogen $Q_M$ adsorbed for an identical weight of pure crystal into the total amount of nitrogen $Q_X$ adsorbed by the bed $(X = (Q_X/Q_M).100)$.

12. The method according to claim 11, further including the step of calculating the weight percent water Y of the molecular sieve based on the activity parameter X, and correlations with activity which were determined by a least squares technique for molecular sieve types 5AMG and MG3 respectively as follows:

$$Y = -1.9621500 + 23.338246889.e(-0.0247605280.X)$$

$$Y = -0.7140699 + 29.679412844.e(-0.037272280.X).$$

* * * * *

UNITED STATES PATENT AND TRADEMARK OFFICE
CERTIFICATE OF CORRECTION

PATENT NO. : 4,916,630
DATED : April 10, 1990
INVENTOR(S) : George W. Miller

It is certified that error appears in the above-identified patent and that said Letters Patent is hereby corrected as shown below:

IN THE ABSTRACT, line 8, "seive" should be ---sieve---.
IN THE ABSTRACT, line 25, "squres" should be ---squares---.
IN THE ABSTRACT, line 27, "square" should be ---squares---.
Col 4, line 1, "of" should be ---or---.
Col 4, line 23, "crystals" should be ---crystal---.
Col 7, line 12, "millimeters" should be ---milliliters---.
Col 8, line 30, equation 8, "r" should be ---R---.
Col 10, line 42, "step-by" should be ---step-by-step---.
Col 12, line 18, "the" should be ---The---.
Col 12, line 21, "as" should be ---gas---.
Col 12, line 42, "selectove" should be ---selector---.
Col 13, line 24, first occurrence of "the" should be ---The---.
Col 41, claim 7, line 62, "hellium" should be ---helium---.
Col 42, line 65, "$P_n = (P_{na}/14.7).760$" should be ---$P_n = (P_{na}/14.7) \cdot 760$---.

Col 43, line 6, "$M_h = (P_{hi} \cdot V_{hi})/(R.T_{hi})$" should be ---$M_h = (P_{hi} \cdot V_{hi})/(R \cdot T_{hi})$---.

Col 43, line 8, "$M_n$" should be ---$M_h$---.

UNITED STATES PATENT AND TRADEMARK OFFICE
CERTIFICATE OF CORRECTION

PATENT NO. : 4,916,630

DATED : April 10, 1990

INVENTOR(S) : George W. Miller

It is certified that error appears in the above-identified patent and that said Letters Patent is hereby corrected as shown below:

Col 43, line 12, "$V_t = (M_h.R.T_{hf})/P_{hf}$" should be
---$V_t = (M_h \cdot R \cdot T_{hf})/P_{hf}$---.

Col 43, line 24, "$V_\beta = (W_x.0.8.V_x)/1000$" should be
---$V_\beta = (W_x \cdot 0.8 \cdot V_x)/1000$---.

Col 43, line 39, "$Q_n = (a.P_n^c)/(1+b.P_n^c)$" should be
---$Q_n = (a \cdot P_n^c)/(1+b \cdot P_n^c)$---.

Col 43, line 41, "absorbed" should read ---absorbed;---.

Col 43, line 44, "$W_n = M_n.280134$" should be
---$W_n = M_n \cdot 280134$---.

Col 43, line 55, "$Q_x = (\Delta W.R.273.15).1000$" should be
---$Q_x = (\Delta W \cdot R \cdot 273.15) \cdot 1000$---.

Col 43, line 63, "$Q_M = Q_n.W_x.0.8$" should be
---$Q_M = Q_n \cdot W_x \cdot 0.8$---.

UNITED STATES PATENT AND TRADEMARK OFFICE
CERTIFICATE OF CORRECTION

PATENT NO. : 4,916,630

DATED : April 10, 1990

INVENTOR(S) : George W. Miller

It is certified that error appears in the above-identified patent and that said Letters Patent is hereby corrected as shown below:

Col 44, line 5, "$X = (Q_X/Q_M).100$" should be
---$X = (Q_X/Q_M) \cdot 100$---.

Col 44, claim 8, line 13, "$\vec{\leftarrow}$" should be --- + ---.

Col 44, claim 9, line 12, "$M_h = (P_{hi} \cdot V_{hi})/(R \cdot T_{hi});$"
should be ---$M_h = (P_{hi} \cdot V_{hi})/(R \cdot T_{hi});$---.

Col 44, claim 9, line 21, "$V_t = (M_h \cdot R \cdot T_{hf})/P_{hf}.$"
should be ---$V_t = (M_h \cdot R \cdot T_{hf})/P_{hf}.$---.

Col 45, line 18, "$W_n = ((P_{nb} \cdot V_v)/(R \cdot T_n)).28.0134$"
should be ---$W_n = ((P_{nb} \cdot V_v)/(R \cdot T_n)) \cdot 28.0134$---.

Col 45, line 31, "$Q_X = (\Delta W.R.273.15).1000$" should be
---$Q_X = (\Delta W \cdot R \cdot 273.15) \cdot 1000$---.

Col 45, line 41, "$Q_M = Q_n.W_x.0.8$" should be
---$Q_M = Q_n \cdot W_x \cdot 0.8$---.

UNITED STATES PATENT AND TRADEMARK OFFICE
CERTIFICATE OF CORRECTION

PATENT NO. : 4,916,630  
DATED : April 10, 1990  
INVENTOR(S) : George W. Miller Page 4 of 5

It is certified that error appears in the above-identified patent and that said Letters Patent is hereby corrected as shown below:

Col 45, line 48, "$(X = (Q_X/Q_M).100).$" should be
---$(X = (Q_X/Q_M) \cdot 100).$---.

Col 46, line 63, "$M_h = (P_{hi} \cdot V_{hi})/(R \cdot T_{hi})$" should be
---$M_h = (P_{hi} \cdot V_{hi})/(R \cdot T_{hi})$---.

Col 46, line 65, "$V_t = (M_h.R.T_{hf})/P_{hf}$" should be
---$V_t = (M_h \cdot R \cdot T_{hf})/P_{hf}$---.

Col 47, line 23, "$W_n = ((P_{nb}.V_v)/(R.T_n)).28.0134$" should be
---$W_n = ((P_{nb} \cdot V_v)/(R \cdot T_n)) \cdot 28.0134$---.

Col 48, line 4, "$Q_X = (\Delta W.R.273.15).1000$" should be
---$Q_X = (\Delta W \cdot R \cdot 273.15) \cdot 1000$---.

Col 48, line 14, "$Q_M = Q_n.W_x.0.8$" should be
---$Q_M = Q_n \cdot W_x \cdot 0.8$---.

Col 48, line 21, "$(X = (Q_X/Q_M).100).$" should be
---$(X = (Q_X/Q_M) \cdot 100).$---.

UNITED STATES PATENT AND TRADEMARK OFFICE
CERTIFICATE OF CORRECTION

PATENT NO. : 4,916,630

DATED : April 10, 1990

INVENTOR(S) : George W. Miller

It is certified that error appears in the above-identified patent and that said Letters Patent is hereby corrected as shown below:

Col 48, line 29,

"Y = -1.9621500 + 23.338246889.e(-0.0247605280.X)" should be ---Y = -1.9621500 + 23.338246889·e(-0.0247605280·X)---.

Col 48, line 31,

"Y = -0.7140699 + 29.679412844.e(-0.037272280.X)." should be ---Y = -0.7140699 + 29.679412844·e(-0.037272280·X).---.

Signed and Sealed this

Thirty-first Day of December, 1991

Attest:

HARRY F. MANBECK, JR.

*Attesting Officer*   *Commissioner of Patents and Trademarks*